Figure 1:
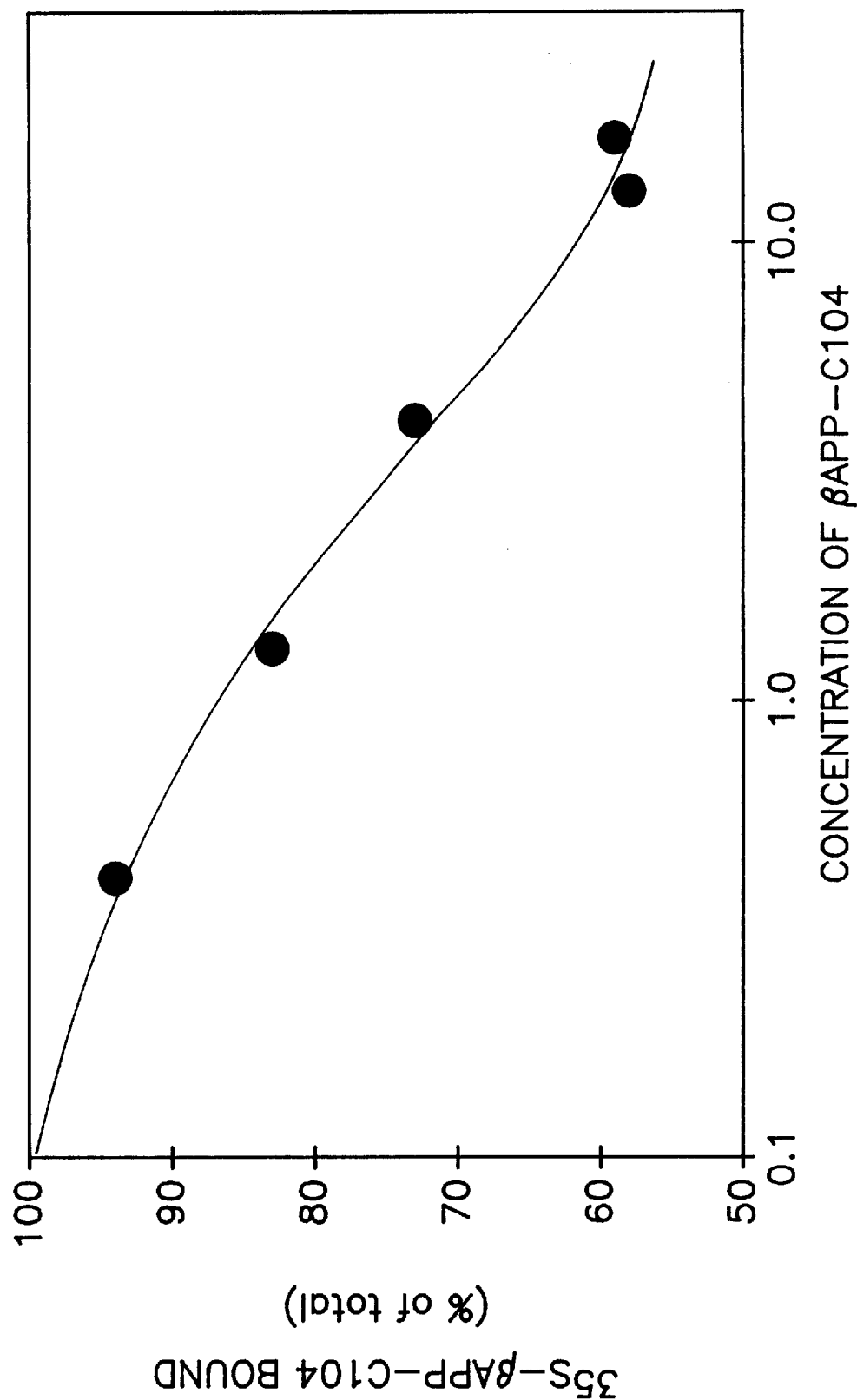

US005854392A

United States Patent [19]
Manly et al.

[11] Patent Number: 5,854,392
[45] Date of Patent: Dec. 29, 1998

[54] β APP-C100 RECEPTOR

[75] Inventors: Susan P. Manly, Wallingford; Michael R. Kozlowski, Noank, both of Conn.; Rachael L. Neve, Belmont, Mass.

[73] Assignees: Bristol-Myers Squibb Company, New York, N.Y.; McLean Hospital Corporation, Belmont, Mass.

[21] Appl. No.: 114,555

[22] Filed: Aug. 30, 1993

Related U.S. Application Data

[63] Continuation-in-part of Ser. No. 938,184, Aug. 31, 1992, abandoned.
[51] Int. Cl.$^6$ .................................................. C07K 14/435
[52] U.S. Cl. .......................... 530/350; 530/327; 530/395; 435/69.1; 536/23.5
[58] Field of Search ................................. 530/350, 395, 530/327; 435/69.1; 536/23.5

[56] References Cited

U.S. PATENT DOCUMENTS 4,675,285   6/1987   Clark et al. .................. 435/6

OTHER PUBLICATIONS

Thomas et al., Methods In Enzymology, vol. 182, 499–505, 1990, Academic Press, Inc.
Kozlowski et al., The Journal of Neuroscience, vol. 12, pp. 1679, 1992.
Gearing et al., The Embo J., vol. 8, pp. 3667, 1989.
Roth, M. et al., 1966, "Correlation Between Scores for Dementia and Counts of 'Senile Plaques' in Cerebral Grey Matter of Elderly Subjects" Nature 209:109–110.
Terry, R.D. et al., 1981, "Some Morphometric Aspects of the Brain in Senile Dementia of the Alzheimer Type" Annals of Neurology 10:184–192.
Glenner, G.G., 1983, "Alzheimer's Disease" Arch. Pathol. Lab. Med. 107:281–282.
Schonfeld, A.R. and Katzman, R., 1983, "In Vivo Cholinotrophic Activities" Banbury Report 15, Cold Spring Harbor Lab., Cold Spring Harbor, N.Y.
Glenner, G.G. and Wong, C.W., 1984, "Alzheimer's Disease: Initial Report of the Purification and Characterization of a Novel Cerebrovascular Amyloid Protein" Biochem. Biophs. Res. Comm. 120:885–890.

Masters, C.L. et al., 1985, "Amyloid Plaque Core Protein in Alzheimer Disease and Down Syndrome" Proc. Natl. Acad. Sci. USA 82:4245–4249.
Selkoe, D.J. et al., 1988, "β–Amyloid Precursor Protein of Alzheimer Disease Occurs as 110–to–135–kilodalton Membrane–associated Proteins in Neural and Non–neural Tissues" Proc. Natl. Acad. Sci. USA 85:7341–7345.
Yakner, B.A. et al., 1989, "Neurotoxicity of a Fragment of the Amyloid Precursor Associated with Alzheimer's Disease" Science 245:417–420.
Wolf, D. et al., 1990, "Identification and Characterization of C–terminal Fragments of the β–Amyloid Precursor Produced in Cell Culture" EMBO J. 9:2079–2084.
Maruyama, K. et al., 1990, "Formation of Amyloid–like Fibrils in COS Cells Overexpressing Part of the Alzheimer Amyloid Protein Precursor" Science 347:566–569.
Estus, S. et al., 1992, "Potentially Amyloidogenic, Carboxyl–Terminal Derivatives of the Amyloid Protein Precursor" Science 255:726–728.
Neve, R.L., 1992, "Brain Transplants of Cells Expressing the Carboxyl–terminal Fragment of the Alzheimer Amyloid Protein Precursor Cause Specific Neuropathology In Vivo" Proc. Natl. Acad. Sci. USA 89:3448–3452.
Iacopino, A. et al., 1992, "Calbindin–$D_{28K}$–containing Neurons in Animal Models of Neurodegeneration: Possible Protection From Excitotoxicity" Mol. Brain Res. 13:251–261.
Mattson, M.P. et al., 1992 "β–Amyloid Peptides Destabilize Calcium Homeostatis and Render Human Cortical Neurons Vulnerable to Excitotoxicity" J. Neuroscience 12:376–389.
Joseph, R. and Han, E., 1992, "Amyloid β–Protein Fragment 25–35 Causes Activation of Cytoplasmic Calcium in Neurons" Biochem. Biophys. Res. Comm. 184:1441–1447.

*Primary Examiner*—Sally P. Teng
*Attorney, Agent, or Firm*—Pennie & Edmonds LLP

[57] ABSTRACT

The present invention relates to the cloning of βAPP-C100 receptor (C100-R), and genetically engineered host cells which express the C100-R. Such engineered cells may be used to evaluate and screen drugs and analogs of β-APP involved in Alzheimer's Disease.

7 Claims, 19 Drawing Sheets

```
CCC CCT CGA GGT CGA CTC CTG GAG CCC GTC AGT ATC GGC GGA ATT    45
 P   P   R   G   R   L   L   E   P   V   S   I   G   G   I

CCT GAA CAA TGG GCT CGA CTG CTC CAA ACC TCC AAC ATT ACA AAA    90
 P   E   Q   W   A   R   L   L   Q   T   S   N   I   T   K

CTG GAA CAG AAG AAG AAC CCA CAG GCT GTT CTG GAT GTT CTC GAG   135
 L   E   Q   K   K   N   P   Q   A   V   L   D   V   L   E
                                                         *
TTT TAC GAC TCC AAA GAA ACA GTC AAC AAC CAG AAA TAC ATG AGC   180
 F   Y   D   S   K   E   T   V   N   N   Q   K   Y   M   S

TTT ACA TCA GGA GAT AAA AGT GCC CAT GGA TAT ATA GCA GCA CAT   225
 F   T   S   G   D   K   S   A   H   G   Y   I   A   A   H

CAG TCG AAT ACC AAA ACA GCT TCA GAA CCT CCT TTG GCT CCT CCT   270
 Q   S   N   T   K   T   A   S   E   P   P   L   A   P   P

GTA TCT GAA GAA GAG GAT GAA GAA GAG GAA GAG GAA GAA GAT GAT   315
 V   S   E   E   E   D   E   E   E   E   E   E   E   D   D

AAT GAG CCC CCG CCT GTC ATT GCA CCA AGA CCA GAG CAT ACA AAA   360
 N   E   P   P   P   V   I   A   P   R   P   E   H   T   K

TCA ATC TAT ACT CGT TCT GTG GTT GAG TCA ATT GCT TCA CCA GCA   405
 S   I   Y   T   R   S   V   V   E   S   I   A   S   P   A

GCA CCA AAT AAA GAA GCC ACC CCA CCT TCT GCT GAG AAT GCC AAT   450
 A   P   N   K   E   A   T   P   P   S   A   E   N   A   N

TCC AGT ACT TTG TAC AGG AAT ACA GAT CGG CAA AGA AAA AAA TCC   495
 S   S   T   L   Y   R   N   T   D   R   Q   R   K   K   S

AAG ATG ACA GAT GAG GAG ATC CTA GAG AAG CTA AGA AGC ATT GTG   540
 K   M   T   D   E   E   I   L   E   K   L   R   S   I   V

AGT GTT GGG GAC CCA AAG AAG AAA TAT ACA AGA TTT GAA AAA ATT   585
 S   V   G   D   P   K   K   K   Y   T   R   F   E   K   I

GGC CAA GGG GCA TCA GGA ACT GTT TAC ACA GCA CTA GAC ATT GCG   630
 G   Q   G   A   S   G   T   V   Y   T   A   L   D   I   A

ACA GGA CAA GAG GTG GCT ATA AAG CAA ATG AAC CTT CAA CAG CAG   675
 T   G   Q   E   V   A   I   K   Q   M   N   L   Q   Q   Q
```

FIG.4A

```
CCC AAA AAG GAA TTA ATT ATT AAT GAA ATT CTT GTC ATG AGG GAA    720
 P   K   K   E   L   I   I   N   E   I   L   V   M   R   E

AAT AAG AAC CCC AAT ATT GTC AAT TAT TTA GAT AGC TAC TTA GTG    765
 N   K   N   P   N   I   V   N   Y   L   D   S   Y   L   V

GGT GAT GAA CTG TGG GTA GTC ATG GAA TAC TTG GCT GGT GGC TCT    810
 G   D   E   L   W   V   V   M   E   Y   L   A   G   G   S

TTG ACT GAC GTG GTC ACA GAA ACC TGT ATG GAT GAA GGA CAG ATA    855
 L   T   D   V   V   T   E   T   C   M   D   E   G   Q   I

GCA GCC GTC TGT AGA GAG TGC CTC CAA GCT TTG GAT TTC TTG CAC    900
 A   A   V   C   R   E   C   L   Q   A   L   D   F   L   H

TCA AAA CAA GTG ATC CAC AGA GAT ATA AAG AGT GAC AAT ATT CTC    945
 S   K   Q   V   I   H   R   D   I   K   S   D   N   I   L

CTC GGG ATG GAT GGT TCT GTT AAA CTG ACT GAT TTT GGA TTC TGT    990
 L   G   M   D   G   S   V   K   L   T   D   F   G   F   C

GCC CAA ATC ACT CCT GAG CAA AGT AAA CGA AGC ACT ATG GTG GGA    1035
 A   Q   I   T   P   E   Q   S   K   R   S   T   M   V   G

ACT CCC TAT TGG ATG GCA CCT GAG GTG GTA ACT CGA AAA GCT TAT    1080
 T   P   Y   W   M   A   P   E   V   V   T   R   K   A   Y

GGC CCG AAA GTT GAT ATC TGG TCT CTG GGA ATC ATG GCC ATT GAA    1125
 G   P   K   V   D   I   W   S   L   G   I   M   A   I   E

ATG GTG GAA GGT GAA CCC CCT TAC CTT AAT GAA AAT CCA CTC AGG    1170
 M   V   E   G   E   P   P   Y   L   N   E   N   P   L   R

GCC TTA TAT CTG ATA GCC ACT AAT GGA ACC CCA GAG CTC CAG AAT    1215
 A   L   Y   L   I   A   T   N   G   T   P   E   L   Q   N

CCC GAG AGA CTG TCA GCT GTA TTC CGT GAC TTC TTA AAT CGC TGT    1260
 P   E   R   L   S   A   V   F   R   D   F   L   N   R   C

CTT GAG ATG GAT GTG GAT AGA CGA GGG TCT GCC AAG GAG CTT TTG    1305
 L   E   M   D   V   D   R   R   G   S   A   K   E   L   L

CAG CAT CCA TTT TTA AAA TTA GCC AAG CCC CTG TCC AGC CTC ACT    1350
 Q   H   P   F   L   K   L   A   K   P   L   S   S   L   T
```

FIG.4B

```
CCT CTG ATT CTT GCT GCA AAG GAA GCC ATT AAG AAC AGT AGC CGT   1395
 P   L   I   L   A   A   K   E   A   I   K   N   S   S   R

TAG AAG TGC AAG CCT TAC CCC TCA CCG TCT CCC GGA TGA GTA AGA   1440
 *

CTG AAC TAA AAC TCT GCT GCA GGA TCC ACA GAA GAA AAG ACA GTC   1485

AAA TGG AGT GGG GGT TCT TTA ACT TTC AAG TGA ATA GAA ACT TCT   1530

TAT AAA CCT TTT TCC TAC TCC CTC AGA TTA TGT AAT TTA TTT GTA   1575

AGC CTG AAC CGC AGC CCA CAC AGG GCA GCA ATG TCG AAG TAG CCA   1620

TTA AGT GGC CAC TTC CAC CGT GAA GCG AGA GAG CCA GTA GTG AAT   1665

CCC CTC ATT CGT GCA TTT ACT TTG AAG AAA AAG AGA TTT CTC AAA   1710

GAT GCA CAC TCC CTC TTC ATA GTG CTG TGT GTT TTT AAG TTA GAG   1755

AGT AGT CCC CCT TCC ATT CAA ACC TCT TTC AAA ATC CCT TAC CCA   1800

ACG TGA TGT TTT TTC ACT TGC ATT GTC ATT AGA TGT CCA GAA AAA   1845

AAG ATG TCA AAA TGT TTT TTT TAA AAA AAA GAA AGC AAA AAA GCA   1890

AAG AAA AAA GGA ATT CCA GCT GAG CGC CGG TCG CTA CCA TTA CCA   1935

GTT GGT CTG GTG TCA AGC GGC CGC CAC CGC GGT GGA               1971
```

FIG.4C

RATBCCAIS RAT CALCIUM CHANNEL ALPHA-1 SUBUNIT mRNA, co 112    71    71
76.7% IDENTITY IN 30 nt OVERLAP

```
              460       470       480       490       500       510
t7.dam  CAGGAATACAGATCGGCAAAGAAAAAAATCCAAGATGACAGATGAGGAGATCCTAGAGAA
                                  X::::::::  ::  ::   : :  :::::::::X
RATBCC  GATCATCATCACCTTCCAGGAGCAGGGAGACAAGATGATGGAAGAATACAGCCTAGAGAA
              4380      4390      4400      4410      4420      4430

520       530       540       550       560       570
t7.dam  GCTAAGAACATTGTGNGTGTTGGGGACCCAAAGAAGANNNTATACAAGATTTGAAAAAAT RATBCC  AAATGAGAGGGCCTGCATCGACTTTGCCATCAGTGCCAAGCCGCTGACCAGGCACATGCC
              4440      4450      4460      4470      4480      4490
```

FIG.5A

MUSCRP55 MOUSE mRNA FOR CALRETICULIN
78.0% IDENTITY IN 50 nt OVERLAP

```
              250       260       270       280       290       300
t7.dam  TTCAGAACCTCCTTTGGCTCCTCCTGTATCTGAAGAAGAGGATGAAGAAGAGGAAGAGGA
                                  X:::::  ::::::  ::::::::::  ::   ::::
MUSCRP  TGAGGATAAAGAGGATGATGATGACAGAGATGAAGATGAGGACGAAGAAGATGAGAAGGA
              1220      1230      1240      1250      1260      1270

310       320       330       340       350       360
t7.dam  AGAAGATGATAATGAGCCCCGCCTGTCATTGCACCAAGACCAGAGCATACAAAATAATCT
              ::::::::::X   :   ::   :::
MUSCRP  GGAAGATGAGGAAGAATCCCCTGGCCAAGCCAAGGATGAGCTGTAGAGGCCACACCACCT
              1280      1290      1300      1310      1320      1330
```

RATCALRET RAT mRNA FOR CALRETICULIN
77.6% IDENTITY IN 49 nt OVERLAP

```
              250       260       270       280       290       300
t7.dam  TTCAGAACCTCCTTTGGCTCCTCCTGTATCTGAAGAAGAGGATGAAGAAGAGGAAGAGGA
                                  X:::::  ::  :::::::::  ::  ::   ::::
RATCAL  CGAGGATAAAGAGGATGAGGATGACAGAGATGAAGATGAAGATGAGGATGAGAAGGA
              1190      1200      1210      1220      1230      1240

310       320       330       340       350       360
t7.dam  AGAAGATGATAATGAGCCCCGCCTGTCATTGCACCAAGACCAGAGCATACAAAATAATCT
              ::::::::::X   :   ::   :::
RATCAL  AGAAGATGAGGAGGATGCCACTGGCCAAGCCAAGGATGAGCTGTAGAGGCCACACCACCT
              1250      1260      1270      1280      1290      1300
```

FIG.5B

A35041 — *RYANODINE RECEPTOR — HUMAN
 15.7% IDENTITY IN 178 aa OVERLAP

```
                                          10        20        30
t7tran                           PPRGRLLEPVSIGGIPEQWARLLQTSNITKL
                                 ...::  ..........  .::  ..  .
A35041   GVGVTTSLRPPHHFSPPCFVAALPAAGAAEAPARLSPAIPLEALRDKALRMLGEAVRDGG
             1770      1780      1790      1800      1810      1820

40        50        60        70        80        90
t7tran   EQKKNPQAVLDVLEFYDSKETVNNQKYMSFTSGDKSAHGYIAAHQSEYQTASEPPLAPPV
         .. ...: ..   ...:    . :..   :...  ....  .       V.. . ...^  .
A35041   QHARDPVGASVEFQFVPVLKLVSTLLVMGIFGDEDVKQILKMIEPEVFTEEEEEEDEEEE
             1830      1840      1850      1860      1870      1880

100       110       120       130       140
t7tran   SEEEDEEEEEEEDDNEPRLSLHQDQSIQNNLYSSVVESIASPAAPNKEATHL-LLRCQ-F
         :::::::::::  .V......  ..   ^  .. :.....  . :  .. :  .::.  .
A35041   GEEEDEEEKEEDEEETAQEKEDEEKEEEEAAEGEKEEGLEEGLLQMKLPESVKLQMCHLL
             1890      1900      1910      1920      1930      1940

150       160       170       180       190       200
t7tran   QYF-DRNTDRQRKKSKMTDEEILEKLRTLPVLGTQRRFYTRFEKIGQGASGTVYTALDIA
         .::  :...  ... ..       .:  ......:
A35041   EYFCDQELQHRVESLAAFAERYVDKLQANQRSRYGLLIKAFSMTAAETARRTREFRSPPQ
             1950      1960      1970      1980      1990      2000
```

FIG.5C

```
HUMRYR  HUMAN RYANODINE RECEPTOR mRNA, COMPLETE cds.   113   79   87
 57.0% IDENTITY IN 135 nt OVERLAP
              250       260       270       280       290       300
t7.dam   TCAGAACCTCCTTTGGCTCCTCCTGTATCTGAAGAAGAGGATGAAGAAGAGGAAGAGGAA
                                    :: X:::::::: : :: ::: :  ::: ::
HUMRYR   ACAGCACAGGAAAAGGAAGATGAGGAAAAAGAGGAAGAGGAGGCAGCAGAAGGGCAGAAA
              5800      5810      5820      5830      5840      5850

310       320       330       340       350       360
t7.dam   GAAGATGATAATGAGCCCCGCCTGTCATTGCACCAAG--ACCAGAGCATACAAAATAATC
         ::::X :         :::     : ::: :      :  :::  ::::::: :  :: : :
HUMRYR   GAAGAAGGCTTGGAGGAAGGGCTG-CTCCAGATGAAGTTGCCAGAGTCTGTGAAGTTACA
              5860      5870      5880      5890      5900      5910

370       380       390       400       410       420
t7.dam   TATACTCGTCTGTGGTTGAGTCAATTGCT-TCACCAGCAGCACCAAATAAAGAAGCCACC
              ::    :    :  :: : ::::  ::: :: :  ::::  :::   ::
HUMRYR   GATGTGCCAC-CTGCTGGAGT--ATTTCTGTGACCAAGAGCTGCAGCACCGTGTGGAGTC
              5920      5930      5940      5950      5960      5970

430       440       450       460       470       480
t7.dam   CACCTTCTGCTGAGATGCCAATTCCAGTACTTTGACAGGAATACAGATCGGCAAAGAAAA HUMRYR   CCTGGCAGCCTTTGCGGAGCGCTATGTGGACAAGCTCCAGGCCAACCAGCGGAGCCGCTA
              5980      5990      6000      6010      6020      6030
```

FIG.5D

S04654 - RYANODINE RECEPTOR - RABBIT            63   63   9
15.7% IDENTITY IN 178 aa OVERLAP
                                    10         20         30
t7tran                      PPRGRLLEPVSIGGIPEQWARLLQTSNITKL
                            ...::  ..........  ::  ..   .
S04654  GVGVTTSLRPPHHFSPPCFVAALPAAGVAEAPARLSPAIPLEALRDKALRMLGEAVRDGG
             1770      1780      1790      1800      1810      1820

40        50        60        70        80        90
t7tran  EQKKNPQAVLDVLEFYDSKETVNNQKYMSFTSGDKSAHGYIAAHQSEYQTASEPPLAPPV
        .. ...: .   ..:  . :..    :...  ... .  V.. . ...  ^     .
S04654  QHARDPVGGSVEFQFVPVLKLVSTLLVMGIFGDEDVKQILKMIEPEVFTEEEEEEEEEE
             1830      1840      1850      1860      1870      1880

100       110       120       130       140
t7tran  SEEEDEEEEEEEDDNEPRLSLHQDQSIQNNLYSSVVESIASPAAPNKEATHL-LLRCQ-F
        .::::::::::::   .:  ..... ...  ..  :....  V. :  ... ^  ::  .
S04654  EEEEEEEDEEEKEEDEEEEEKEDAEKEEEEAPEGEKEDLEEGLLQMKLPESVKLQMCNLL
             1890      1900      1910      1920      1930      1940

150       160       170       180       190       200
t7tran  QYF-DRNTDRQRKKSKMTDEEILEKLRTLPVLGTQRRFYTRFEKIGQGASGTVYTALDIA
        .::  ...  .   .: . ....:
S04654  EYFCDQELQHRVESLAAFAERYVDKLQANQRSRYALLMRAFTMSAAETARRTREFRSPPQ
             1950      1960      1970      1980      1990      2000

FIG.5E

EcoRI
                                                    ├─┐
  1   CTGGTAATGG TAGCGACCGG CGCTCACGTG GAATTCGAGA CTGCTAGATT CGTCCCTGCC
      GACCATTACC ATCGCTGGCC GCGAGTGCAC CTTAAGCTCT GACGATCTAA GCAGGGACGG

61   AGCGTGCTCC GAGGTACTGG AAAGGTCTTG GCAGGGTGGC TGGACCCTTG GCAGGAGCTG
      TCGCACGAGG CTCCATGACC TTTCCAGAAC CGTCCCACCG ACCTGGGAAC CGTCCTCGAC

121   TGAAATCAGC TGCAACTGAA AATGTCTGAC AGCTTGGATA ACGAAGAAAA ACCTCCAGCT
      ACTTTAGTCG ACGTTGACTT TTACAGACTG TCGAACCTAT TGCTTCTTTT TGGAGGTCGA

181   CCCCCACTGA GGATGAACAG TAACAACCGA GATTCTTCAG CACTCAACCA CAGCTCCAAA
      GGGGGTGACT CCTACTTGTC ATTGTTGGCT CTAAGAAGTC GTGAGTTGGT GTCGAGGTTT

241   CCACTGCCCA TGCGCCCGGA AGAGAAGAAT AAGAAAGCCA GGCTTCGCTC TATCTTCCCA
      GGTGACGGGT ACGCGGGCCT TCTCTTCTTA TTCTTTCGGT CCGAAGCGAG ATAGAAGGGT

301   GGAGGAGGGG ATAAAACCAA TAAGAAGAAA GAGAAAGAAC GCCCAGAGAT CTCTCTTCCT
      CCTCCTCCCC TATTTTGGTT ATTCTTCTTT CTCTTTCTTG CGGGTCTCTA GAGAGAAGGA

EcoRI
                                                              ├─┐
361   TCAGACTTTG AGCATACGAT TCATGTGGGT TTTGATGCAG TCACCGGCGA ATTCACTCCA
      AGTCTGAAAC TCGTATGCTA AGTACACCCA AAACTACGTC AGTGGCCGCT TAAGTGAGGT

421   GATCTCTATG GCTCACAGAT GTGCCCAGGA AGCTCCAGAG GGAATTCCTG AACAATGGGC
      CTAGAGATAC CGAGTGTCTA CACGGGTCCT TCGAGGTCTC CCTTAAGGAC TTGTTACCCG

481   TCGACTGCTC CAAACCTCCA ACATTACAAA ACTGGAACAG AAGAAGAACC CACAGGCTGT
      AGCTGACGAG GTTTGGAGGT TGTAATGTTT TGACCTTGTC TTCTTCTTGG GTGTCCGACA

541   TCTGGATGTT CTCAAGTTTT ACGACTCCAA AGAAACAGTC AACAACCAGA AATACATGAG
      AGACCTACAA GAGTTCAAAA TGCTGAGGTT TCTTTGTCAG TTGTTGGTCT TTATGTACTC

601   CTTTACATCA GGAGATAAAA GTGCCCATGG ATATATAGCA GCACATCAGT CGAATACCAA
      GAAATGTAGT CCTCTATTTT CACGGGTACC TATATATCGT CGTGTAGTCA GCTTATGGTT

661   AACAGCTTCA GAACC
      TTGTCGAAGT CTTGG

FIG.9

```
  1 GAATTCACAC ATGATCTTCT GGGCTCCTCC AAAGGGCTGG CATTACTTTT CTAGCTCTAC
       N  S  H  M  I  F  W  A  P  P  K  G  W  H  Y  F  S  S  S

61 CCTCTGTAGC ACTCTAAGCT CAGGTCGTCC TCCTCCTACC ACTGCTGCTG CTGTGATCGC
       T  L  C  S  T  L  S  S  G  R  P  P  P  T  A  A  A  V  I

121 CTATCCCCTC TCATCCTCCT TCCTCGCCAA TTTCTGCTCC TCCTCCCGCA TCCCGCTCCT
       A  Y  P  L  S  S  F  L  A  N  F  C  S  S  S  R  I  P  L

181 CCAGCAGCTA AAGGCAGAAC TTCGGCAGCA GCTTTCCTTC TCTCCTGCCA CGAAGAGATT
       L  Q  Q  L  K  A  E  L  R  Q  Q  L  S  F  S  P  A  T  K  R

241 GGAACAGCCC AGTACACCGG CCCATCTGAG TTCACTTTGC ATCTCAATTT TGTTCTTCAA
       L  E  Q  P  S  T  P  A  H  L  S  S  L  G  I  S  I  L  F  F

301 CATATTTGAT CCTCTGCCAG CTTTGAGTCA TCTTCAGACG TGGAGCTGTG AAAATCAGCT
       N  I  F  D  P  L  P  A  L  S  H  L  Q  T  W  S  C  E  N  Q

361 GCAACTGAAA ATGTCTGACA GCTTGGATAA CGAAGAAAAA CCTCCAGCTC CCACTGAGGA
       L  Q  L  K  M  S  D  S  L  D  N  E  E  K  P  P  A  P  T  E

421 TGACAGTAAC ACCGAGATTC TTCAGCACTC AACCACAGCT CCAAACCACT GCCCATGCGC
       D  D  S  N  T  E  I  L  Q  H  S  T  T  A  P  N  H  G  P  C

481 CCGGAAGAGA AGAATAAGAA AGCCAGGCTT CGCTCTATCT TCCCAGGAGG AGGGGATAAA
       A  R  K  R  R  I  R  K  P  G  F  A  L  S  Q  E  E  G  I

541 ACCAATAAGA AGAAAGAGAA AGAACGCCCA GAGATCTCTC TTCCTTCAGA CTTTGAGCAT
       K  P  I  R  R  K  R  K  N  A  Q  R  S  L  F  L  Q  T  L  S

601 ACGATTCATG TGGGTTTTGA TGCAGTCACC GGGGAATTCA CTCCAGATCT CTATGGCTCA
       I  R  F  M  W  V  L  M  Q  S  P  G  N  S  L  Q  I  S  M  A

661 CAGATGTGCC CAGGAAGCTC CAGAGGGAAT TCCTGAACAA TGGGCTCGAC TGCTCCAAAC
       H  R  C  A  Q  E  A  P  E  G  I  P  E  Q  W  A  R  L  L  Q
```

FIG.10

HABIR #1 #4

1   GGAATTCTGC CAGTTTATTA CAGAGGACGA TAAATGATTC CATGTGGATA GGGCATAACA
    CCTTAAGACG GTCAAATAAT GTCTCCTGCT ATTTACTAAG GTACACCTAT CCCGTATTGT

61  TACAGAGAAT GAGACTATGC CAGA
    ATGTCTCTTA CTCTGATACG GTCT

1 #1 T3

1   GGAATTCCCA GTGGAAACCA AATGAAACGA CTTTGNCTTG TNGAGGGGGA AGAATGTGAA
    CCTTAAGGGT CACCTTTGGT TTACTTTGCT GAAACNGAAC ANCTCCCCCT TCTTACACTT

61  MAAAAAACAA AAGCAAAATG ACCCGCCCAC AAGATACAAC AGAAACCCCA TCCACTACCC
    KTTTTTTGTT TTCGTTTTAC TGGGCGGGTG TTCTATGTTG TCTTTGGGGT AGGTGATGGG

121 ATCCCTTCCA TGTGAGGCCG ACCACCCAGG CCCCAACACC CT
    TAGGGAAGGT ACACTCCGGC TGGTGGGTCC GGGGTTGTGG GA

4.t3

1   GGAATTCCAA TAAGAAGAAG GAGAAAGAGC GCCCAGAGAT CTCTCTTCCT TCAGACTTTG
    CCTTAAGGTT ATTCTTCTTC CTCTTTCTCG CGGGTCTCTA GAGAGAAGGA AGTCTGAAAC

61  AGCATACGAT TCATGTGGGG TTGATGCAGT CACCGGGAAT TCACTCCAGA
    TCGTATGCTA AGTACACCCC AACTACGTCA GTGGCCCTTA AGTGAGGTCT

FIG.11

```
  1 aataagaagaaggagaaagagcgcccagagatctctcttccttcagactt  50
    ||||||||||| ||||||| ||||||||||||||||||||||||||||||
544 aataagaagaaagagaaagaacgcccagagatctctcttccttcagactt 593

51 tgagcatacgattcatgtggg.gttgatgcagtcacc.gggaattcactc  98
    |||||||||||||||||||||  |||||||||||||| ||||||||||||
594 tgagcatacgattcatgtgggttttgatgcagtcaccggggaattcactc 643

99 caga 102
    ||||
644 caga 647
```

FIG.12A

```
 11 ttacagaggacgataaatgattccatgtggatagggcataacat  54
    |||||  |  ||||||| |  |||||  |||  |||  ||||
182 ttacatcaggagataaaagtgcccatggatatatagcagcacat 225
```

FIG.12B

```
 53 naaaaaacaaaagcaaaa   70
    :|||||| ||||||||||
1868 aaaaaaaagaaagcaaaa 1885
```

FIG.12C

SEQUENCE LISTING ( 1 ) GENERAL INFORMATION:

( i i i ) NUMBER OF SEQUENCES: 18

( 2 ) INFORMATION FOR SEQ ID NO:1:

( i ) SEQUENCE CHARACTERISTICS:
        ( A ) LENGTH: 1971 base pairs
        ( B ) TYPE: nucleic acid
        ( C ) STRANDEDNESS: double
        ( D ) TOPOLOGY: unknown ( i i ) MOLECULE TYPE: cDNA ( i x ) FEATURE:
        ( A ) NAME/KEY: CDS
        ( B ) LOCATION: 1..1398

( x i ) SEQUENCE DESCRIPTION: SEQ ID NO:1:

```
CCC  CCT  CGA  GGT  CGA  CTC  CTG  GAG  CCC  GTC  AGT  ATC  GGC  GGA  ATT  CCT         48
Pro  Pro  Arg  Gly  Arg  Leu  Leu  Glu  Pro  Val  Ser  Ile  Gly  Gly  Ile  Pro
 1              5                        10                       15

GAA  CAA  TGG  GCT  CGA  CTG  CTC  CAA  ACC  TCC  AAC  ATT  ACA  AAA  CTG  GAA         96
Glu  Gln  Trp  Ala  Arg  Leu  Leu  Gln  Thr  Ser  Asn  Ile  Thr  Lys  Leu  Glu
              20                        25                       30

CAG  AAG  AAG  AAC  CCA  CAG  GCT  GTT  CTG  GAT  GTT  CTC  GAG  TTT  TAC  GAC        144
Gln  Lys  Lys  Asn  Pro  Gln  Ala  Val  Leu  Asp  Val  Leu  Glu  Phe  Tyr  Asp
         35                        40                       45

TCC  AAA  GAA  ACA  GTC  AAC  AAC  CAG  AAA  TAC  ATG  AGC  TTT  ACA  TCA  GGA        192
Ser  Lys  Glu  Thr  Val  Asn  Asn  Gln  Lys  Tyr  Met  Ser  Phe  Thr  Ser  Gly
     50                        55                       60

GAT  AAA  AGT  GCC  CAT  GGA  TAT  ATA  GCA  GCA  CAT  CAG  TCG  AAT  ACC  AAA        240
Asp  Lys  Ser  Ala  His  Gly  Tyr  Ile  Ala  Ala  His  Gln  Ser  Asn  Thr  Lys
 65                        70                       75                        80

ACA  GCT  TCA  GAA  CCT  CCT  TTG  GCT  CCT  CCT  GTA  TCT  GAA  GAA  GAG  GAT        288
Thr  Ala  Ser  Glu  Pro  Pro  Leu  Ala  Pro  Pro  Val  Ser  Glu  Glu  Glu  Asp
              85                        90                       95
```

| | | | | | | | | | | | | | | | | |
|---|---|---|---|---|---|---|---|---|---|---|---|---|---|---|---|---|
| GAA | GAA | GAG | GAA | GAG | GAA | GAA | GAT | GAT | AAT | GAG | CCC | CCG | CCT | GTC | ATT | 336 |
| Glu | Glu | Glu | Glu | Glu | Glu | Glu | Asp | Asp | Asn | Glu | Pro | Pro | Pro | Val | Ile | |
| | | | 100 | | | | | 105 | | | | | 110 | | | |
| GCA | CCA | AGA | CCA | GAG | CAT | ACA | AAA | TCA | ATC | TAT | ACT | CGT | TCT | GTG | GTT | 384 |
| Ala | Pro | Arg | Pro | Glu | His | Thr | Lys | Ser | Ile | Tyr | Thr | Arg | Ser | Val | Val | |
| | | 115 | | | | | 120 | | | | | 125 | | | | |
| GAG | TCA | ATT | GCT | TCA | CCA | GCA | GCA | CCA | AAT | AAA | GAA | GCC | ACC | CCA | CCT | 432 |
| Glu | Ser | Ile | Ala | Ser | Pro | Ala | Ala | Pro | Asn | Lys | Glu | Ala | Thr | Pro | Pro | |
| 130 | | | | | 135 | | | | | 140 | | | | | | |
| TCT | GCT | GAG | AAT | GCC | AAT | TCC | AGT | ACT | TTG | TAC | AGG | AAT | ACA | GAT | CGG | 480 |
| Ser | Ala | Glu | Asn | Ala | Asn | Ser | Ser | Thr | Leu | Tyr | Arg | Asn | Thr | Asp | Arg | |
| 145 | | | | | 150 | | | | | 155 | | | | | 160 | |
| CAA | AGA | AAA | AAA | TCC | AAG | ATG | ACA | GAT | GAG | GAG | ATC | CTA | GAG | AAG | CTA | 528 |
| Gln | Arg | Lys | Lys | Ser | Lys | Met | Thr | Asp | Glu | Glu | Ile | Leu | Glu | Lys | Leu | |
| | | | | 165 | | | | | 170 | | | | | 175 | | |
| AGA | AGC | ATT | GTG | AGT | GTT | GGG | GAC | CCA | AAG | AAG | AAA | TAT | ACA | AGA | TTT | 576 |
| Arg | Ser | Ile | Val | Ser | Val | Gly | Asp | Pro | Lys | Lys | Lys | Tyr | Thr | Arg | Phe | |
| | | | 180 | | | | | 185 | | | | | 190 | | | |
| GAA | AAA | ATT | GGC | CAA | GGG | GCA | TCA | GGA | ACT | GTT | TAC | ACA | GCA | CTA | GAC | 624 |
| Glu | Lys | Ile | Gly | Gln | Gly | Ala | Ser | Gly | Thr | Val | Tyr | Thr | Ala | Leu | Asp | |
| | | 195 | | | | | 200 | | | | | 205 | | | | |
| ATT | GCG | ACA | GGA | CAA | GAG | GTG | GCT | ATA | AAG | CAA | ATG | AAC | CTT | CAA | CAG | 672 |
| Ile | Ala | Thr | Gly | Gln | Glu | Val | Ala | Ile | Lys | Gln | Met | Asn | Leu | Gln | Gln | |
| 210 | | | | | 215 | | | | | 220 | | | | | | |
| CAG | CCC | AAA | AAG | GAA | TTA | ATT | ATT | AAT | GAA | ATT | CTT | GTC | ATG | AGG | GAA | 720 |
| Gln | Pro | Lys | Lys | Glu | Leu | Ile | Ile | Asn | Glu | Ile | Leu | Val | Met | Arg | Glu | |
| 225 | | | | | 230 | | | | | 235 | | | | | 240 | |
| AAT | AAG | AAC | CCC | AAT | ATT | GTC | AAT | TAT | TTA | GAT | AGC | TAC | TTA | GTG | GGT | 768 |
| Asn | Lys | Asn | Pro | Asn | Ile | Val | Asn | Tyr | Leu | Asp | Ser | Tyr | Leu | Val | Gly | |
| | | | 245 | | | | | 250 | | | | | 255 | | | |
| GAT | GAA | CTG | TGG | GTA | GTC | ATG | GAA | TAC | TTG | GCT | GGT | GGC | TCT | TTG | ACT | 816 |
| Asp | Glu | Leu | Trp | Val | Val | Met | Glu | Tyr | Leu | Ala | Gly | Gly | Ser | Leu | Thr | |
| | | | 260 | | | | | 265 | | | | | 270 | | | |
| GAC | GTG | GTC | ACA | GAA | ACC | TGT | ATG | GAT | GAA | GGA | CAG | ATA | GCA | GCC | GTC | 864 |
| Asp | Val | Val | Thr | Glu | Thr | Cys | Met | Asp | Glu | Gly | Gln | Ile | Ala | Ala | Val | |
| | | 275 | | | | | 280 | | | | | 285 | | | | |
| TGT | AGA | GAG | TGC | CTC | CAA | GCT | TTG | GAT | TTC | TTG | CAC | TCA | AAA | CAA | GTG | 912 |
| Cys | Arg | Glu | Cys | Leu | Gln | Ala | Leu | Asp | Phe | Leu | His | Ser | Lys | Gln | Val | |
| | 290 | | | | | 295 | | | | | 300 | | | | | |
| ATC | CAC | AGA | GAT | ATA | AAG | AGT | GAC | AAT | ATT | CTC | CTC | GGG | ATG | GAT | GGT | 960 |
| Ile | His | Arg | Asp | Ile | Lys | Ser | Asp | Asn | Ile | Leu | Leu | Gly | Met | Asp | Gly | |
| 305 | | | | | 310 | | | | | 315 | | | | | 320 | |
| TCT | GTT | AAA | CTG | ACT | GAT | TTT | GGA | TTC | TGT | GCC | CAA | ATC | ACT | CCT | GAG | 1008 |
| Ser | Val | Lys | Leu | Thr | Asp | Phe | Gly | Phe | Cys | Ala | Gln | Ile | Thr | Pro | Glu | |
| | | | | 325 | | | | | 330 | | | | | 335 | | |
| CAA | AGT | AAA | CGA | AGC | ACT | ATG | GTG | GGA | ACT | CCC | TAT | TGG | ATG | GCA | CCT | 1056 |
| Gln | Ser | Lys | Arg | Ser | Thr | Met | Val | Gly | Thr | Pro | Tyr | Trp | Met | Ala | Pro | |
| | | | 340 | | | | | 345 | | | | | 350 | | | |
| GAG | GTG | GTA | ACT | CGA | AAA | GCT | TAT | GGC | CCG | AAA | GTT | GAT | ATC | TGG | TCT | 1104 |
| Glu | Val | Val | Thr | Arg | Lys | Ala | Tyr | Gly | Pro | Lys | Val | Asp | Ile | Trp | Ser | |
| | | 355 | | | | | 360 | | | | | 365 | | | | |
| CTG | GGA | ATC | ATG | GCC | ATT | GAA | ATG | GTG | GAA | GGT | GAA | CCC | CCT | TAC | CTT | 1152 |
| Leu | Gly | Ile | Met | Ala | Ile | Glu | Met | Val | Glu | Gly | Glu | Pro | Pro | Tyr | Leu | |
| | 370 | | | | | 375 | | | | | 380 | | | | | |
| AAT | GAA | AAT | CCA | CTC | AGG | GCC | TTA | TAT | CTG | ATA | GCC | ACT | AAT | GGA | ACC | 1200 |
| Asn | Glu | Asn | Pro | Leu | Arg | Ala | Leu | Tyr | Leu | Ile | Ala | Thr | Asn | Gly | Thr | |
| 385 | | | | | 390 | | | | | 395 | | | | | 400 | |
| CCA | GAG | CTC | CAG | AAT | CCC | GAG | AGA | CTG | TCA | GCT | GTA | TTC | CGT | GAC | TTC | 1248 |
| Pro | Glu | Leu | Gln | Asn | Pro | Glu | Arg | Leu | Ser | Ala | Val | Phe | Arg | Asp | Phe | |
| | | | | 405 | | | | | 410 | | | | | 415 | | |

| | | | | | | | | | | | | | | | | |
|---|---|---|---|---|---|---|---|---|---|---|---|---|---|---|---|---|
| TTA | AAT | CGC | TGT | CTT | GAG | ATG | GAT | GTG | GAT | AGA | CGA | GGG | TCT | GCC | AAG | 1296 |
| Leu | Asn | Arg | Cys | Leu | Glu | Met | Asp | Val | Asp | Arg | Arg | Gly | Ser | Ala | Lys | |
| | | | 420 | | | | | 425 | | | | | 430 | | | |
| GAG | CTT | TTG | CAG | CAT | CCA | TTT | TTA | AAA | TTA | GCC | AAG | CCC | CTG | TCC | AGC | 1344 |
| Glu | Leu | Leu | Gln | His | Pro | Phe | Leu | Lys | Leu | Ala | Lys | Pro | Leu | Ser | Ser | |
| | | | 435 | | | | | 440 | | | | | 445 | | | |
| CTC | ACT | CCT | CTG | ATT | CTT | GCT | GCA | AAG | GAA | GCC | ATT | AAG | AAC | AGT | AGC | 1392 |
| Leu | Thr | Pro | Leu | Ile | Leu | Ala | Ala | Lys | Glu | Ala | Ile | Lys | Asn | Ser | Ser | |
| | | | 450 | | | | | 455 | | | | | 460 | | | |

| | | | | | |
|---|---|---|---|---|---|
| CGT | TAGAAGTGCA | AGCCTTACCC | CTCACCGTCT | CCCGGATGAG | TAAGACTGAA | 1445 |
| Arg | | | | | |
| 465 | | | | | |

| | | | | | |
|---|---|---|---|---|---|
| CTAAAACTCT | GCTGCAGGAT | CCACAGAAGA | AAAGACAGTC | AAATGGAGTG | GGGGTTCTTT | 1505 |
| AACTTTCAAG | TGAATAGAAA | CTTCTTATAA | ACCTTTTCC | TACTCCCTCA | GATTATGTAA | 1565 |
| TTTATTTGTA | AGCCTGAACC | GCAGCCCACA | CAGGGCAGCA | ATGTCGAAGT | AGCCATTAAG | 1625 |
| TGGCCACTTC | CACCGTGAAG | CGAGAGAGCC | AGTAGTGAAT | CCCCTCATTC | GTGCATTTAC | 1685 |
| TTTGAAGAAA | AAGAGATTTC | TCAAAGATGC | ACACTCCCTC | TTCATAGTGC | TGTGTGTTTT | 1745 |
| TAAGTTAGAG | AGTAGTCCCC | CTTCCATTCA | AACCTCTTTC | AAAATCCCTT | ACCCAACGTG | 1805 |
| ATGTTTTTTC | ACTTGCATTG | TCATTAGATG | TCCAGAAAAA | AAGATGTCAA | AATGTTTTTT | 1865 |
| TTAAAAAAAA | GAAAGCAAAA | AAGCAAAGAA | AAAAGGAATT | CCAGCTGAGC | GCCGGTCGCT | 1925 |
| ACCATTACCA | GTTGGTCTGG | TGTCAAGCGG | CCGCCACCGC | GGTGGA | | 1971 |

(2) INFORMATION FOR SEQ ID NO:2:

(i) SEQUENCE CHARACTERISTICS:
        (A) LENGTH: 465 amino acids
        (B) TYPE: amino acid
        (D) TOPOLOGY: linear (ii) MOLECULE TYPE: protein (xi) SEQUENCE DESCRIPTION: SEQ ID NO:2:

| | | | | | | | | | | | | | | |
|---|---|---|---|---|---|---|---|---|---|---|---|---|---|---|
| Pro | Pro | Arg | Gly | Arg | Leu | Leu | Glu | Pro | Val | Ser | Ile | Gly | Gly | Ile | Pro |
| 1 | | | | 5 | | | | | 10 | | | | | 15 | |
| Glu | Gln | Trp | Ala | Arg | Leu | Leu | Gln | Thr | Ser | Asn | Ile | Thr | Lys | Leu | Glu |
| | | | 20 | | | | | 25 | | | | | 30 | | |
| Gln | Lys | Lys | Asn | Pro | Gln | Ala | Val | Leu | Asp | Val | Leu | Glu | Phe | Tyr | Asp |
| | | | 35 | | | | | 40 | | | | | 45 | | |
| Ser | Lys | Glu | Thr | Val | Asn | Asn | Gln | Lys | Tyr | Met | Ser | Phe | Thr | Ser | Gly |
| | | 50 | | | | | 55 | | | | | 60 | | | |
| Asp | Lys | Ser | Ala | His | Gly | Tyr | Ile | Ala | Ala | His | Gln | Ser | Asn | Thr | Lys |
| 65 | | | | | 70 | | | | | 75 | | | | | 80 |
| Thr | Ala | Ser | Glu | Pro | Pro | Leu | Ala | Pro | Pro | Val | Ser | Glu | Glu | Glu | Asp |
| | | | | 85 | | | | | 90 | | | | | 95 | |
| Glu | Glu | Glu | Glu | Glu | Glu | Glu | Asp | Asp | Asn | Glu | Pro | Pro | Pro | Val | Ile |
| | | | | 100 | | | | | 105 | | | | | 110 | |
| Ala | Pro | Arg | Pro | Glu | His | Thr | Lys | Ser | Ile | Tyr | Thr | Arg | Ser | Val | Val |
| | | | 115 | | | | | 120 | | | | | 125 | | |
| Glu | Ser | Ile | Ala | Ser | Pro | Ala | Ala | Pro | Asn | Lys | Glu | Ala | Thr | Pro | Pro |
| | | | 130 | | | | | 135 | | | | | 140 | | |
| Ser | Ala | Glu | Asn | Ala | Asn | Ser | Ser | Thr | Leu | Tyr | Arg | Asn | Thr | Asp | Arg |
| 145 | | | | | 150 | | | | | 155 | | | | | 160 |
| Gln | Arg | Lys | Lys | Ser | Lys | Met | Thr | Asp | Glu | Glu | Ile | Leu | Glu | Lys | Leu |
| | | | | 165 | | | | | 170 | | | | | 175 | |

| | | | | | | | | | | | | | | |
|---|---|---|---|---|---|---|---|---|---|---|---|---|---|---|
| Arg | Ser | Ile | Val 180 | Ser | Val | Gly | Asp | Pro 185 | Lys | Lys | Tyr | Thr 190 | Arg | Phe |
| Glu | Lys | Ile 195 | Gly | Gln | Gly | Ala | Ser 200 | Gly | Thr | Val | Tyr 205 | Thr | Ala | Leu | Asp |
| Ile | Ala 210 | Thr | Gly | Gln | Glu | Val 215 | Ala | Ile | Lys | Gln | Met 220 | Asn | Leu | Gln | Gln |
| Gln 225 | Pro | Lys | Lys | Glu | Leu 230 | Ile | Ile | Asn | Glu | Ile 235 | Leu | Val | Met | Arg | Glu 240 |
| Asn | Lys | Asn | Pro | Asn 245 | Ile | Val | Asn | Tyr | Leu 250 | Asp | Ser | Tyr | Leu 255 | Val | Gly |
| Asp | Glu | Leu | Trp 260 | Val | Val | Met | Glu | Tyr 265 | Leu | Ala | Gly | Gly 270 | Ser | Leu | Thr |
| Asp | Val | Val 275 | Thr | Glu | Thr | Cys | Met 280 | Asp | Glu | Gly | Gln 285 | Ile | Ala | Ala | Val |
| Cys | Arg 290 | Glu | Cys | Leu | Gln | Ala 295 | Leu | Asp | Phe | Leu | His 300 | Ser | Lys | Gln | Val |
| Ile 305 | His | Arg | Asp | Ile | Lys 310 | Ser | Asp | Asn | Ile | Leu 315 | Leu | Gly | Met | Asp | Gly 320 |
| Ser | Val | Lys | Leu | Thr 325 | Asp | Phe | Gly | Phe | Cys 330 | Ala | Gln | Ile | Thr | Pro 335 | Glu |
| Gln | Ser | Lys | Arg 340 | Ser | Thr | Met | Val | Gly 345 | Thr | Pro | Tyr | Trp | Met 350 | Ala | Pro |
| Glu | Val | Val 355 | Thr | Arg | Lys | Ala | Tyr 360 | Gly | Pro | Lys | Val | Asp 365 | Ile | Trp | Ser |
| Leu | Gly 370 | Ile | Met | Ala | Ile | Glu 375 | Met | Val | Glu | Gly | Glu 380 | Pro | Pro | Tyr | Leu |
| Asn 385 | Glu | Asn | Pro | Leu | Arg 390 | Ala | Leu | Tyr | Leu | Ile 395 | Ala | Thr | Asn | Gly | Thr 400 |
| Pro | Glu | Leu | Gln | Asn 405 | Pro | Glu | Arg | Leu | Ser 410 | Ala | Val | Phe | Arg | Asp 415 | Phe |
| Leu | Asn | Arg | Cys 420 | Leu | Glu | Met | Asp | Val 425 | Asp | Arg | Arg | Gly | Ser 430 | Ala | Lys |
| Glu | Leu | Leu 435 | Gln | His | Pro | Phe | Leu 440 | Lys | Leu | Ala | Lys | Pro 445 | Leu | Ser | Ser |
| Leu | Thr 450 | Pro | Leu | Ile | Leu | Ala 455 | Ala | Lys | Glu | Ala | Ile 460 | Lys | Asn | Ser | Ser |
| Arg 465 | | | | | | | | | | | | | | | |

( 2 ) INFORMATION FOR SEQ ID NO:3:

( i ) SEQUENCE CHARACTERISTICS:
        ( A ) LENGTH: 120 base pairs
        ( B ) TYPE: nucleic acid
        ( C ) STRANDEDNESS: double
        ( D ) TOPOLOGY: unknown ( i i ) MOLECULE TYPE: DNA ( x i ) SEQUENCE DESCRIPTION: SEQ ID NO:3:

| | | | | | |
|---|---|---|---|---|---|
| GATCATCATC | ACCTTCCAGG | AGCAGGGAGA | CAAGATGATG | GAAGAATACA | GCCTAGAGAA | 60 |
| AAATGAGAGG | GCCTGCATCG | ACTTTGCCAT | CAGTGCCAAG | CCGCTGACCA | GGCACATGCC | 120 |

( 2 ) INFORMATION FOR SEQ ID NO:4:

( i ) SEQUENCE CHARACTERISTICS:
        ( A ) LENGTH: 120 base pairs
        ( B ) TYPE: nucleic acid (C) STRANDEDNESS: double
(D) TOPOLOGY: unknown (ii) MOLECULE TYPE: DNA (xi) SEQUENCE DESCRIPTION: SEQ ID NO:4:

```
TGAGGATAAA GAGGATGATG ATGACAGAGA TGAAGATGAG GACGAAGAAG ATGAGAAGGA    60
GGAAGATGAG GAAGAATCCC CTGGCCAAGC CAAGGATGAG CTGTAGAGGC CACACCACCT   120
```

(2) INFORMATION FOR SEQ ID NO:5:

(i) SEQUENCE CHARACTERISTICS:
(A) LENGTH: 120 base pairs
(B) TYPE: nucleic acid
(C) STRANDEDNESS: double
(D) TOPOLOGY: unknown (ii) MOLECULE TYPE: DNA (xi) SEQUENCE DESCRIPTION: SEQ ID NO:5:

```
CGAGGATAAA GAGGATGAGG ATGACAGAGA TGAAGATGAA GATGAAGAGG ATGAGAAGGA    60
AGAAGATGAG GAGGATGCCA CTGGCCAAGC CAAGGATGAG CTGTAGAGGC CACACCACCT   120
```

(2) INFORMATION FOR SEQ ID NO:6:

(i) SEQUENCE CHARACTERISTICS:
(A) LENGTH: 240 amino acids
(B) TYPE: amino acid
(C) STRANDEDNESS: single
(D) TOPOLOGY: unknown (ii) MOLECULE TYPE: protein (xi) SEQUENCE DESCRIPTION: SEQ ID NO:6:

```
Gly Val Gly Val Thr Thr Ser Leu Arg Pro Pro His His Phe Ser Pro
 1               5                  10                  15

Pro Cys Phe Val Ala Ala Leu Pro Ala Ala Gly Ala Ala Glu Ala Pro
             20                  25                  30

Ala Arg Leu Ser Pro Ala Ile Pro Leu Glu Ala Leu Arg Asp Lys Ala
         35                  40                  45

Leu Arg Met Leu Gly Glu Ala Val Arg Asp Gly Gln His Ala Arg
     50                  55                  60

Asp Pro Val Gly Ala Ser Val Glu Phe Gln Phe Val Pro Val Leu Lys
 65                  70                  75                  80

Leu Val Ser Thr Leu Leu Val Met Gly Ile Phe Gly Asp Glu Asp Val
                 85                  90                  95

Lys Gln Ile Leu Lys Met Ile Glu Pro Glu Val Phe Thr Glu Glu Glu
                100                 105                 110

Glu Glu Glu Asp Glu Glu Glu Glu Gly Glu Glu Glu Asp Glu Glu Glu
            115                 120                 125

Lys Glu Glu Asp Glu Glu Glu Thr Ala Gln Glu Lys Glu Asp Glu Glu
        130                 135                 140

Lys Glu Glu Glu Glu Ala Ala Glu Gly Glu Lys Glu Glu Gly Leu Glu
145                 150                 155                 160

Glu Gly Leu Leu Gln Met Lys Leu Pro Glu Ser Val Lys Leu Gln Met
                165                 170                 175

Cys His Leu Leu Glu Tyr Phe Cys Asp Gln Glu Leu Gln His Arg Val
                180                 185                 190

Glu Ser Leu Ala Ala Phe Ala Glu Arg Tyr Val Asp Lys Leu Gln Ala
            195                 200                 205
```

```
    Asn  Gln  Arg  Ser  Arg  Tyr  Gly  Leu  Leu  Ile  Lys  Ala  Phe  Ser  Met  Thr
         210                 215                      220

Ala  Ala  Glu  Thr  Ala  Arg  Arg  Thr  Arg  Glu  Phe  Arg  Ser  Pro  Pro  Gln
    225                      230                      235                      240
```

( 2 ) INFORMATION FOR SEQ ID NO:7:

( i ) SEQUENCE CHARACTERISTICS:
        ( A ) LENGTH: 236 base pairs
        ( B ) TYPE: nucleic acid
        ( C ) STRANDEDNESS: double
        ( D ) TOPOLOGY: unknown ( i i ) MOLECULE TYPE: DNA ( x i ) SEQUENCE DESCRIPTION: SEQ ID NO:7:

```
ACAGCACAGG  AAAAGGAAGA  TGAGGAAAAA  GAGGAAGAGG  AGGCAGCAGA  AGGGGAGAAA        60

GAAGAAGGCT  TGGAGGAAGG  GCTGCTCCAG  ATGAAGTTGC  CAGAGTCTGT  GAAGTTACAG       120

ATGTGCCACC  TGCTGGAGTA  TTTCTGTGAC  CAAGAGCTGC  AGCACCGTGT  GGAGTCCCTG       180

GCAGCCTTTG  CGGAGCGCTA  TGTGGACAAG  CTCCAGGCCA  ACCAGCGGAG  CCGCTA           236
```

( 2 ) INFORMATION FOR SEQ ID NO:8:

( i ) SEQUENCE CHARACTERISTICS:
        ( A ) LENGTH: 240 amino acids
        ( B ) TYPE: amino acid
        ( C ) STRANDEDNESS: single
        ( D ) TOPOLOGY: unknown ( i i ) MOLECULE TYPE: protein ( x i ) SEQUENCE DESCRIPTION: SEQ ID NO:8:

```
    Gly  Val  Gly  Val  Thr  Thr  Ser  Leu  Arg  Pro  Pro  His  His  Phe  Ser  Pro
    1               5                    10                       15

Pro  Cys  Phe  Val  Ala  Ala  Leu  Pro  Ala  Ala  Gly  Val  Ala  Glu  Ala  Pro
                   20                   25                       30

Ala  Arg  Leu  Ser  Pro  Ala  Ile  Pro  Leu  Glu  Ala  Leu  Arg  Asp  Lys  Ala
              35                        40                       45

Leu  Arg  Met  Leu  Gly  Glu  Ala  Val  Arg  Asp  Gly  Gln  His  Ala  Arg
         50                        55                   60

Asp  Pro  Val  Gly  Gly  Ser  Val  Glu  Phe  Gln  Phe  Val  Pro  Val  Leu  Lys
    65                  70                        75                            80

Leu  Val  Ser  Thr  Leu  Leu  Val  Met  Gly  Ile  Phe  Gly  Asp  Glu  Asp  Val
                        85                        90                  95

Lys  Gln  Ile  Leu  Lys  Met  Ile  Glu  Pro  Glu  Val  Phe  Thr  Glu  Glu  Glu
                        100                      105                      110

Glu  Glu  Glu  Glu  Glu  Glu  Glu  Glu  Glu  Glu  Glu  Glu  Glu  Glu  Glu  Asp
                   115                      120                      125

Glu  Glu  Glu  Lys  Glu  Glu  Asp  Glu  Glu  Glu  Glu  Glu  Lys  Glu  Asp  Ala
              130                      135                      140

Glu  Lys  Glu  Glu  Glu  Glu  Ala  Pro  Glu  Gly  Glu  Lys  Glu  Asp  Leu  Glu
    145                      150                      155                      160

Glu  Gly  Leu  Leu  Gln  Met  Lys  Leu  Pro  Glu  Ser  Val  Lys  Leu  Gln  Met
                        165                      170                      175

Cys  Asn  Leu  Leu  Glu  Tyr  Phe  Cys  Asp  Gln  Glu  Leu  Gln  His  Arg  Val
                        180                      185                      190

Glu  Ser  Leu  Ala  Ala  Phe  Ala  Glu  Arg  Tyr  Val  Asp  Lys  Leu  Gln  Ala
                   195                      200                      205

Asn  Gln  Arg  Ser  Arg  Tyr  Ala  Leu  Leu  Met  Arg  Ala  Phe  Thr  Met  Ser
```

|  | 210 | | | 215 | | | | | 220 | | | | |
|---|---|---|---|---|---|---|---|---|---|---|---|---|---|
| Ala | Ala | Glu | Thr | Ala | Arg | Arg | Thr | Arg | Glu | Phe | Arg | Ser | Pro | Pro | Gln |
| 225 | | | | | 230 | | | | 235 | | | | 240 |

(2) INFORMATION FOR SEQ ID NO:9:

(i) SEQUENCE CHARACTERISTICS:
        (A) LENGTH: 675 base pairs
        (B) TYPE: nucleic acid
        (C) STRANDEDNESS: double
        (D) TOPOLOGY: unknown (ii) MOLECULE TYPE: cDNA (xi) SEQUENCE DESCRIPTION: SEQ ID NO:9:

| CTGGTAATGG | TAGCGACCGG | CGCTCACGTG | GAATTCGAGA | CTGCTAGATT | CGTCCCTGCC | 60 |
|---|---|---|---|---|---|---|
| AGCGTGCTCC | GAGGTACTGG | AAAGGTCTTG | GCAGGGTGGC | TGGACCCTTG | GCAGGAGCTG | 120 |
| TGAAATCAGC | TGCAACTGAA | AATGTCTGAC | AGCTTGGATA | ACGAAGAAAA | ACCTCCAGCT | 180 |
| CCCCCACTGA | GGATGAACAG | TAACAACCGA | GATTCTTCAG | CACTCAACCA | CAGCTCCAAA | 240 |
| CCACTGCCCA | TGCGCCCGGA | AGAGAAGAAT | AAGAAAGCCA | GGCTTCGCTC | TATCTTCCCA | 300 |
| GGAGGAGGGG | ATAAAACCAA | TAAGAAGAAA | GAGAAAGAAC | GCCCAGAGAT | CTCTCTTCCT | 360 |
| TCAGACTTTG | AGCATACGAT | TCATGTGGGT | TTTGATGCAG | TCACCGGGGA | ATTCACTCCA | 420 |
| GATCTCTATG | GCTCACAGAT | GTGCCCAGGA | AGCTCCAGAG | GGAATTCCTG | AACAATGGGC | 480 |
| TCGACTGCTC | CAAACCTCCA | ACATTACAAA | ACTGGAACAG | AAGAAGAACC | CACAGGCTGT | 540 |
| TCTGGATGTT | CTCAAGTTTT | ACGACTCCAA | AGAAACAGTC | AACAACCAGA | AATACATGAG | 600 |
| CTTTACATCA | GGAGATAAAA | GTGCCCATGG | ATATATAGCA | GCACATCAGT | CGAATACCAA | 660 |
| AACAGCTTCA | GAACC | | | | | 675 |

(2) INFORMATION FOR SEQ ID NO:10:

(i) SEQUENCE CHARACTERISTICS:
        (A) LENGTH: 675 base pairs
        (B) TYPE: nucleic acid
        (C) STRANDEDNESS: double
        (D) TOPOLOGY: unknown (ii) MOLECULE TYPE: cDNA (iv) ANTI-SENSE: YES (xi) SEQUENCE DESCRIPTION: SEQ ID NO:10:

| GGTTCTGAAG | CTGTTTTGGT | ATTCGACTGA | TGTGCTGCTA | TATATCCATG | GGCACTTTTA | 60 |
|---|---|---|---|---|---|---|
| TCTCCTGATG | TAAAGCTCAT | GTATTTCTGG | TTGTTGACTG | TTTCTTTGGA | GTCGTAAAAC | 120 |
| TTGAGAACAT | CCAGAACAGC | CTGTGGGTTC | TTCTTCTGTT | CCAGTTTTGT | AATGTTGGAG | 180 |
| GTTTGGAGCA | GTCGAGCCCA | TTGTTCAGGA | ATTCCCTCTG | GAGCTTCCTG | GGCACATCTG | 240 |
| TGAGCCATAG | AGATCTGGAG | TGAATTCCCC | GGTGACTGCA | TCAAAACCCA | CATGAATCGT | 300 |
| ATGCTCAAAG | TCTGAAGGAA | GAGAGATCTC | TGGGCGTTCT | TTCTCTTTCT | TCTTATTGGT | 360 |
| TTTATCCCCT | CCTCCTGGGA | AGATAGAGCG | AAGCCTGGCT | TTCTTATTCT | TCTCTTCCGG | 420 |
| GCGCATGGGC | AGTGGTTTGG | AGCTGTGGTT | GAGTGCTGAA | GAATCTCGGT | TGTTACTGTT | 480 |
| CATCCTCAGT | GGGGGAGCTG | GAGGTTTTTC | TTCGTTATCC | AAGCTGTCAG | ACATTTTCAG | 540 |
| TTGCAGCTGA | TTTCACAGCT | CCTGCCAAGG | GTCCAGCCAC | CCTGCCAAGA | CCTTTCCAGT | 600 |
| ACCTCGGAGC | ACGCTGGCAG | GGACGAATCT | AGCAGTCTCG | AATTCCACGT | GAGCGCCGGT | 660 |
| CGCTACCATT | ACCAG | | | | | 675 |

( 2 ) INFORMATION FOR SEQ ID NO:11:

( i ) SEQUENCE CHARACTERISTICS:
        ( A ) LENGTH: 720 base pairs
        ( B ) TYPE: nucleic acid
        ( C ) STRANDEDNESS: double
        ( D ) TOPOLOGY: unknown ( i i ) MOLECULE TYPE: cDNA ( i x ) FEATURE:
        ( A ) NAME/KEY: CDS
        ( B ) LOCATION: 2..718

( x i ) SEQUENCE DESCRIPTION: SEQ ID NO:11:

```
G AAT TCA CAC ATG ATC TTC TGG GCT CCT CCA AAG GGC TGG CAT TAC        46
  Asn Ser His Met Ile Phe Trp Ala Pro Pro Lys Gly Trp His Tyr
  1               5                  10                   15

TTT TCT AGC TCT ACC CTC TGT AGC ACT CTA AGC TCA GGT CGT CCT CCT      94
Phe Ser Ser Ser Thr Leu Cys Ser Thr Leu Ser Ser Gly Arg Pro Pro
             20                  25                  30

CCT ACC ACT GCT GCT GCT GTG ATC GCC TAT CCC CTC TCA TCC TCC TTC     142
Pro Thr Thr Ala Ala Ala Val Ile Ala Tyr Pro Leu Ser Ser Ser Phe
            35                  40                  45

CTC GCC AAT TTC TGC TCC TCC TCC CGC ATC CCG CTC CTC CAG CAG CTA     190
Leu Ala Asn Phe Cys Ser Ser Ser Arg Ile Pro Leu Leu Gln Gln Leu
            50                  55                  60

AAG GCA GAA CTT CGG CAG CAG CTT TCC TTC TCT CCT GCC ACG AAG AGA     238
Lys Ala Glu Leu Arg Gln Gln Leu Ser Phe Ser Pro Ala Thr Lys Arg
    65                  70                  75

TTG GAA CAG CCC AGT ACA CCG GCC CAT CTG AGT TCA CTT TGC ATC TCA     286
Leu Glu Gln Pro Ser Thr Pro Ala His Leu Ser Ser Leu Cys Ile Ser
80                  85                  90                  95

ATT TTG TTC TTC AAC ATA TTT GAT CCT CTG CCA GCT TTG AGT CAT CTT     334
Ile Leu Phe Phe Asn Ile Phe Asp Pro Leu Pro Ala Leu Ser His Leu
                100                 105                 110

CAG ACG TGG AGC TGT GAA AAT CAG CTG CAA CTG AAA ATG TCT GAC AGC     382
Gln Thr Trp Ser Cys Glu Asn Gln Leu Gln Leu Lys Met Ser Asp Ser
            115                 120                 125

TTG GAT AAC GAA GAA AAA CCT CCA GCT CCC ACT GAG GAT GAC AGT AAC     430
Leu Asp Asn Glu Glu Lys Pro Pro Ala Pro Thr Glu Asp Asp Ser Asn
            130                 135                 140

ACC GAG ATT CTT CAG CAC TCA ACC ACA GCT CCA AAC CAC TGC CCA TGC     478
Thr Glu Ile Leu Gln His Ser Thr Thr Ala Pro Asn His Cys Pro Cys
145                 150                 155

GCC CGG AAG AGA AGA ATA AGA AAG CCA GGC TTC GCT CTA TCT TCC CAG     526
Ala Arg Lys Arg Arg Ile Arg Lys Pro Gly Phe Ala Leu Ser Ser Gln
160                 165                 170                 175

GAG GAG GGG ATA AAA CCA ATA AGA AGA AAG AGA AAG AAC GCC CAG AGA     574
Glu Glu Gly Ile Lys Pro Ile Arg Arg Lys Arg Lys Asn Ala Gln Arg
                180                 185                 190

TCT CTC TTC CTT CAG ACT TTG AGC ATA CGA TTC ATG TGG GTT TTG ATG     622
Ser Leu Phe Leu Gln Thr Leu Ser Ile Arg Phe Met Trp Val Leu Met
            195                 200                 205

CAG TCA CCG GGG AAT TCA CTC CAG ATC TCT ATG GCT CAC AGA TGT GCC     670
Gln Ser Pro Gly Asn Ser Leu Gln Ile Ser Met Ala His Arg Cys Ala
        210                 215                 220

CAG GAA GCT CCA GAG GGA ATT CCT GAA CAA TGG GCT CGA CTG CTC CAA     718
Gln Glu Ala Pro Glu Gly Ile Pro Glu Gln Trp Ala Arg Leu Leu Gln
        225                 230                 235

AC                                                                  720
```

( 2 ) INFORMATION FOR SEQ ID NO:12:

( i ) SEQUENCE CHARACTERISTICS:
    ( A ) LENGTH: 239 amino acids
    ( B ) TYPE: amino acid
    ( D ) TOPOLOGY: linear ( i i ) MOLECULE TYPE: protein ( x i ) SEQUENCE DESCRIPTION: SEQ ID NO:12:

```
Asn  Ser  His  Met  Ile  Phe  Trp  Ala  Pro  Pro  Lys  Gly  Trp  His  Tyr  Phe
 1              5                        10                       15

Ser  Ser  Ser  Thr  Leu  Cys  Ser  Thr  Leu  Ser  Ser  Gly  Arg  Pro  Pro  Pro
              20                        25                       30

Thr  Thr  Ala  Ala  Ala  Val  Ile  Ala  Tyr  Pro  Leu  Ser  Ser  Ser  Phe  Leu
              35                        40                       45

Ala  Asn  Phe  Cys  Ser  Ser  Ser  Arg  Ile  Pro  Leu  Leu  Gln  Gln  Leu  Lys
         50                        55                       60

Ala  Glu  Leu  Arg  Gln  Gln  Leu  Ser  Phe  Ser  Pro  Ala  Thr  Lys  Arg  Leu
 65                       70                        75                       80

Glu  Gln  Pro  Ser  Thr  Pro  Ala  His  Leu  Ser  Ser  Leu  Cys  Ile  Ser  Ile
                   85                        90                       95

Leu  Phe  Phe  Asn  Ile  Phe  Asp  Pro  Leu  Pro  Ala  Leu  Ser  His  Leu  Gln
              100                       105                      110

Thr  Trp  Ser  Cys  Glu  Asn  Gln  Leu  Gln  Leu  Lys  Met  Ser  Asp  Ser  Leu
              115                       120                      125

Asp  Asn  Glu  Glu  Lys  Pro  Pro  Ala  Pro  Thr  Glu  Asp  Asp  Ser  Asn  Thr
         130                       135                      140

Glu  Ile  Leu  Gln  His  Ser  Thr  Thr  Ala  Pro  Asn  His  Cys  Pro  Cys  Ala
145                       150                       155                      160

Arg  Lys  Arg  Arg  Ile  Arg  Lys  Pro  Gly  Phe  Ala  Leu  Ser  Ser  Gln  Glu
              165                       170                      175

Glu  Gly  Ile  Lys  Pro  Ile  Arg  Arg  Lys  Arg  Lys  Asn  Ala  Gln  Arg  Ser
              180                       185                      190

Leu  Phe  Leu  Gln  Thr  Leu  Ser  Ile  Arg  Phe  Met  Trp  Val  Leu  Met  Gln
              195                       200                      205

Ser  Pro  Gly  Asn  Ser  Leu  Gln  Ile  Ser  Met  Ala  His  Arg  Cys  Ala  Gln
     210                       215                      220

Glu  Ala  Pro  Glu  Gly  Ile  Pro  Glu  Gln  Trp  Ala  Arg  Leu  Leu  Gln
225                       230                      235
```

( 2 ) INFORMATION FOR SEQ ID NO:13:

( i ) SEQUENCE CHARACTERISTICS:
    ( A ) LENGTH: 84 base pairs
    ( B ) TYPE: nucleic acid
    ( C ) STRANDEDNESS: double
    ( D ) TOPOLOGY: unknown ( i i ) MOLECULE TYPE: cDNA ( x i ) SEQUENCE DESCRIPTION: SEQ ID NO:13:

GGAATTCTGC CAGTTTATTA CAGAGGACGA TAAATGATTC CATGTGGATA GGGCATAACA        60

TACAGAGAAT GAGACTATGC CAGA        84

( 2 ) INFORMATION FOR SEQ ID NO:14:

( i ) SEQUENCE CHARACTERISTICS:
    ( A ) LENGTH: 84 base pairs
    ( B ) TYPE: nucleic acid (C) STRANDEDNESS: double
(D) TOPOLOGY: unknown (i i) MOLECULE TYPE: cDNA (i v) ANTI-SENSE: YES (x i) SEQUENCE DESCRIPTION: SEQ ID NO:14:

TCTGGCATAG TCTCATTCTC TGTATGTTAT GCCCTATCCA CATGGAATCA TTTATCGTCC    60

TCTGTAATAA ACTGGCAGAA TTCC    84

(2) INFORMATION FOR SEQ ID NO:15:

(i) SEQUENCE CHARACTERISTICS:
        (A) LENGTH: 162 base pairs
        (B) TYPE: nucleic acid
        (C) STRANDEDNESS: double
        (D) TOPOLOGY: unknown (i i) MOLECULE TYPE: cDNA (i x) FEATURE:
    (A) NAME/KEY: misc_feature
    (B) LOCATION: 36
    (D) OTHER INFORMATION: /note= "N=Unknown Nucleotide"

(i x) FEATURE:
    (A) NAME/KEY: misc_feature
    (B) LOCATION: 42
    (D) OTHER INFORMATION: /note= "N=Unknown Nucleotide"

(x i) SEQUENCE DESCRIPTION: SEQ ID NO:15:

GGAATTCCCA GTGGAAACCA AATGAAACGA CTTTGNCTTG TNGAGGGGA AGAATGTGAA    60

MAAAAAACAA AAGCAAAATG ACCCGCCCAC AAGATACAAC AGAAACCCCA TCCACTACCC    120

ATCCCTTCCA TGTGAGGCCG ACCACCCAGG CCCCAACACC CT    162

(2) INFORMATION FOR SEQ ID NO:16:

(i) SEQUENCE CHARACTERISTICS:
        (A) LENGTH: 162 base pairs
        (B) TYPE: nucleic acid
        (C) STRANDEDNESS: double
        (D) TOPOLOGY: unknown (i i) MOLECULE TYPE: cDNA (i v) ANTI-SENSE: YES (i x) FEATURE:
    (A) NAME/KEY: misc_feature
    (B) LOCATION: 121
    (D) OTHER INFORMATION: /note= "N=Unknown Nucleotide"

(i x) FEATURE:
    (A) NAME/KEY: misc_feature
    (B) LOCATION: 127
    (D) OTHER INFORMATION: /note= "N=Unknown Nucleotide"

(x i) SEQUENCE DESCRIPTION: SEQ ID NO:16:

AGGGTGTTGG GGCCTGGGTG GTCGGCCTCA CATGGAAGGG ATGGGTAGTG GATGGGGTTT    60

CTGTTGTATC TTGTGGGCGG GTCATTTGC TTTTGTTTTT TKTTCACATT CTTCCCCCTC    120

NACAAGNCAA AGTCGTTTCA TTTGGTTTCC ACTGGGAATT CC    162

(2) INFORMATION FOR SEQ ID NO:17:

(i) SEQUENCE CHARACTERISTICS:
        (A) LENGTH: 110 base pairs
        (B) TYPE: nucleic acid
        (C) STRANDEDNESS: double (D) TOPOLOGY: unknown (i i) MOLECULE TYPE: cDNA (x i) SEQUENCE DESCRIPTION: SEQ ID NO:17:

GGAATTCCAA  TAAGAAGAAG  GAGAAAGAGC  GCCCAGAGAT  CTCTCTTCCT  TCAGACTTTG         60

AGCATACGAT  TCATGTGGGG  TTGATGCAGT  CACCGGGAAT  TCACTCCAGA                    110

(2) INFORMATION FOR SEQ ID NO:18:

(i) SEQUENCE CHARACTERISTICS:
        (A) LENGTH: 110 base pairs
        (B) TYPE: nucleic acid
        (C) STRANDEDNESS: double
        (D) TOPOLOGY: unknown (i i) MOLECULE TYPE: cDNA (i v) ANTI-SENSE: YES (x i) SEQUENCE DESCRIPTION: SEQ ID NO:18:

TCTGGAGTGA  ATTCCCGGTG  ACTGCATCAA  CCCCACATGA  ATCGTATGCT  CAAAGTCTGA         60

AGGAAGAGAG  ATCTCTGGGC  GCTCTTTCTC  CTTCTTCTTA  TTGGAATTCC                    110

β APP-C100 RECEPTOR

The present application is a continuation-in-part of application Ser. No. 07/938,184, now abandoned, filed Aug. 31, 1992 which is incorporated by reference herein in its entirety.

This invention was made with Government support under Contract #R01 NS 28965 awarded by the National Institutes of Health. Therefore, the government has certain rights in the invention.

TABLE OF CONTENTS
1. INTRODUCTION
2. BACKGROUND OF THE INVENTION
3. SUMMARY OF THE INVENTION
4. BRIEF DESCRIPTION OF THE FIGURES
5. DETAILED DESCRIPTION OF THE INVENTION
   5.1. THE C100-R CODING SEQUENCE
   5.2. EXPRESSION OF THE C100-R
      5.2.1. EXPRESSION SYSTEMS
      5.2.2. IDENTIFICATION OF TRANSFECTANTS OR TRANSFORMANTS THAT EXPRESS THE C100-R
      5.2.3. RECOVERY OF THE C100-R
   5.3. GENERATION OF ANTIBODIES THAT DEFINE THE C100-R
   5.4. ANTI-SENSE RNA AND RIBOZYMES
   5.5. USES OF THE C100-R, DNA AND ENGINEERED CELL LINES
6. EXAMPLES
   6.1. MATERIAL AND METHODS
      6.1.1. IN VITRO TRANSLATION OF FLAG-βAPP-C100
      6.1.2. CELL CULTURE
      6.1.3. BINDING TO CELLS
      6.1.4. BINDING AUTORADIOGRAPHY
      6.1.5. SCREENING FOR THE C100-R cDNA BY EXPRESSION CLONING
      6.1.6. cDNA CHARACTERIZATION
      6.1.7. IN SITU HYBRIDIZATION USING βAPP-C100 BINDING PROTEIN PROBE
      6.1.8. CLONING OF THE FULL LENGTH RAT APP-4
   6.2. RESULTS
      6.2.1. RADIOLIGAND BINDING
      6.2.2. CLONING AND CHARACTERIZATION OF THE C100-R
      6.2.3. IN SITU HYBRIDIZATION
7. EXAMPLE: CLONING OF HUMAN C100-R
8. DEPOSIT OF MICROORGANISMS

1. INTRODUCTION

The present invention relates to the cloning of the receptor, for the carboxy-terminus of the β-amyloid precursor protein (including the amyloid domain), referred to herein as C100-R, and genetically engineered host cells which express the C100-R. Such engineered cells may be used to evaluate and screen drugs and analogs of the β-amyloid precursor protein (β-APP) which may be used for the diagnosis and/or treatment of Alzheimer's Disease.

2. BACKGROUND OF THE INVENTION

Alzheimer's disease is a neurodegenerative disorder that is the most frequent cause of dementia among aged individuals. The disease is characterized by the accumulation of amyloid-containing plaques in the brain, particularly in the temporal cortex and hippocampus and along the walls of the cerebral vasculature (Roch et al., 1966, Nature 209:109–110; Terry et al., 1981, Ann. Neurol. 10:184–192; Glenner G. G., 1983, Arch. Pathol. Lab. Med. 107:281–282; Katzman, R., 1983, Banbury Report 15, Cold Spring Harbor Lab., Cold Spring, N.Y.).

The amyloid peptide (βA4), found in the plaques of the brain derives from a protein referred to as the amyloid (or beta-amyloid) precursor protein (βAPP). βAPP is normally cleaved within the amyloid domain, which lies near its C-terminus, so that no intact amyloid is produced. An alternative processing pathway results in cleavage of βAPP N-terminal to the amyloid domain, releasing the entire C-terminal from which intact amyloid peptide (βA4) of the amyloid protein precursor may be produced (Glenner and Wong, 1984, Biochem Biophys Res. Commun. 120:885–890; Masters et al., 1985, Proc. Natl Acad. Sci. USA 82:4245–4249).

Recent evidence suggests that aberrant processing of β-APP underlies the neuronal degeneration that occurs in Alzheimer's Disease. Neve and coworkers have proposed that the primary βAPP processing event in Alzheimer's Disease is cleavage of the amino terminus of the β/A4 sequence, producing a carboxy-terminal βAPP fragment of 100 amino acid residues (βAPP-C100) which was expressed from a cDNA sequence encoding the carboxyterminal 104 amino acids of βAPP (Yankner et al., 1989, Science 245:417–420). Hereinafter, this fragment of βAPP will be referred to as βAPP-C100 regardless of whether it is expressed from a cDNA encoding the carboxyterminal 100 or 104 amino acid residues of βAPP. Expression of the βAPP-C100 peptide in primate cells has been shown to lead to production of a protein that aggregates and accumulates into deposit-like structures that result in formation of amyloid-like fibrils (Wolf et al., 1990 EMBO J. 9:2079–2084). A retroviral recombinant which directs the expression of βAPP-C100 has also been shown to be neurotoxic when transfected into PC-12 cells that have been induced to differentiate by addition of NGF (nerve growth factor). Furthermore, the conditioned media from these transfected cells is toxic to differentiated neuroblastoma and neural cells, and the neurotoxicity can be removed from the medium by immunoabsorption with an antibody to βAPP-C100 suggesting that βAPP-C100 is secreted by transfected cells and is neurotoxic (Yankner et al., 1989, Science 245:417–420). The toxicity of βAPP-C100 has been further demonstrated by transplantation of cells expressing the peptide into the brains of newborn mice and by creation of mice transgenic for human βAPP-C100 (Neve et al., 1992, Proc. Natl. Acad. Sci. USA 89:3448–3452). Taken together, evidence indicates a role for βAPP-C100 in development of the neurodegeneration in Alzheimer's disease.

Despite the intense interest in the βAPP-C100 peptide, and its biological role in development of Alzheimer's Disease, very little is known about the proteins, receptors or other tissue elements with which the βAPP-C100 peptide interacts to produce neurotoxicity. Very recently, the high affinity binding of βAPP-C100 to the surface of differentiated PC-12 cells has been demonstrated and correlated with neurotoxicity (Kozlowski et al., 1992, J. of Neuroscience 12:1679–1687). Both the binding interaction and the occurrence of the neurotoxic response have the same pH dependence. In addition, in PC-12 cells, both the binding and the susceptibility to neurotoxicity develop with similar time courses during NGF-induced differentiation. Furthermore, a single amino-acid change in the βAPP-C100 peptide (Tyr$_{687}$ to Phe), which eliminates its neurotoxic effect, also produces a loss of binding potency. However, the molecular species responsible for binding has not been identified or characterized. The isolation of a cDNA clone coding for the βAPP-C100 binding site or receptor would facilitate studies aimed at determining the biological function of C100-R and its role in development of Alzheimer's Disease. However, this has not, heretofore, been accomplished.

3. SUMMARY OF THE INVENTION

The present invention relates to the C100-R genes and proteins. The neurotoxic effects, resulting from the interaction between βAPP-C100 and the C100-R suggest that therapeutic applications designed to block this particular receptor/ligand interaction may be useful for treatment of Alzheimer's Disease. The DNA sequences disclosed herein may be engineered into expression systems designed for the production of C100-R and/or cell lines which express the C100-R. Such cell lines may advantageously be used for screening and identifying β-APP analogs, including agonists and antagonists. In accordance with another aspect of the invention, the C100-R DNA, antisense oligonucleotide sequences, or antagonists including antibodies to C100-R may be used in the diagnosis and therapy of Alzheimer's Disease. Transgenic animals containing the C100-R transgene may be used as animal models for the evaluation of β-APP-C100 analogs in vivo.

The invention is based, in part, on the discovery, identification and cloning of a βAPP-C100 binding site that is expressed on the cell surface of neuronally derived cells. The binding site, referred to herein as C100-R, has characteristics indicating that it is involved in mediating the neurotoxic effects of the peptide βAPP-C100.

The invention is also based on the isolation and characterization of a cDNA clone coding for the C100-R which may be of therapeutic value for the diagnoses and design of the drugs for treatment of Alzheimer's Disease.

4. BRIEF DESCRIPTION OF THE FIGURES

FIG. 1. Representative curve showing the inhibition of $^{35}$S-βAPP-C100 binding to (A) NGF-treated (5d) PC12 cells and (B) SK-N-MC cells, by βAPP-C100.

FIG. 2. Representative saturation isotherm (top panel) and Scatchard plot (bottom panel) of $^{35}$S-βAPP-C100 binding to NGF-treated (6d) PC12 cells. The lines were computer generated and represent the best interpretation of the data.

Figure 3:
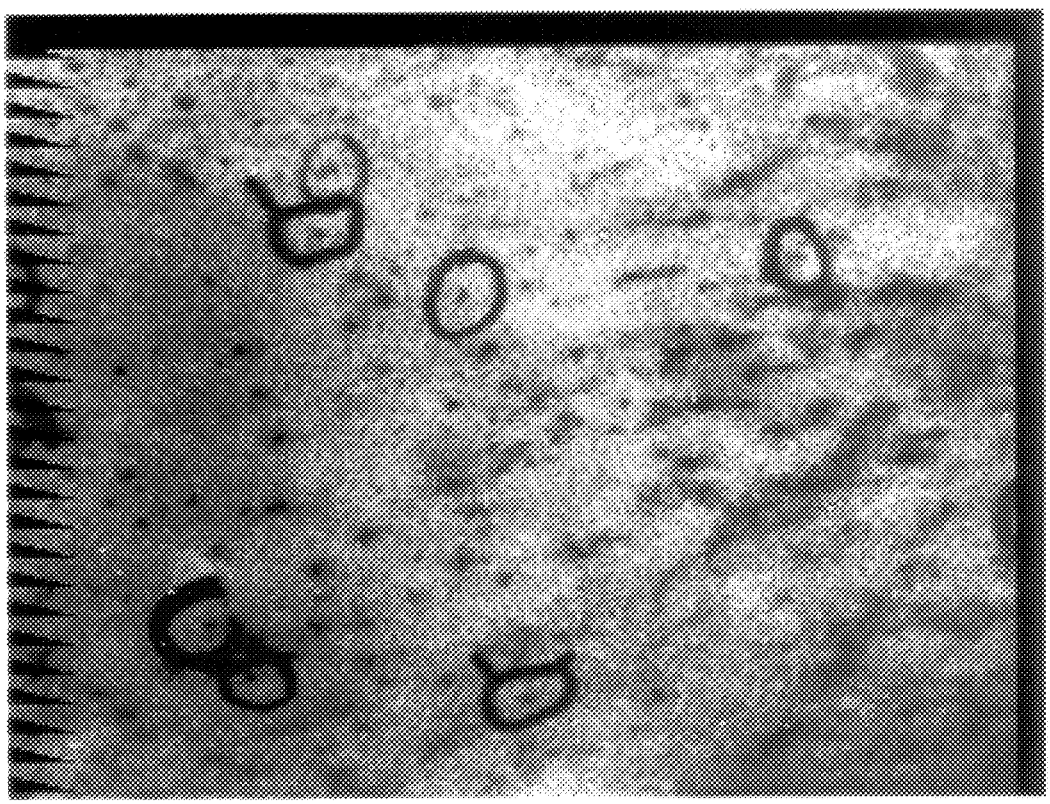

FIG. 3. Screening of λgt11 rat cDNA libraries using the Direct Binding method.

FIG. 4. Nucleotide Sequence of cDNA insert of rat C100-R clone, AB1R [SEQ ID NO: 1]. Underlined region represents SER/THR Kinase "signature" or conserved catalytic core sequence [SEQ ID NO: 2].

FIGS. 5A–C. Sequence homology between C100-R and (A) "B" type calcium channels [SEQ ID NO: 3], (B) calreticulin[SEQ ID NO's : 4 & 5], and (C) Ryanodine calcium channel [SEQ ID NO's: 6–8].

Figure 6:
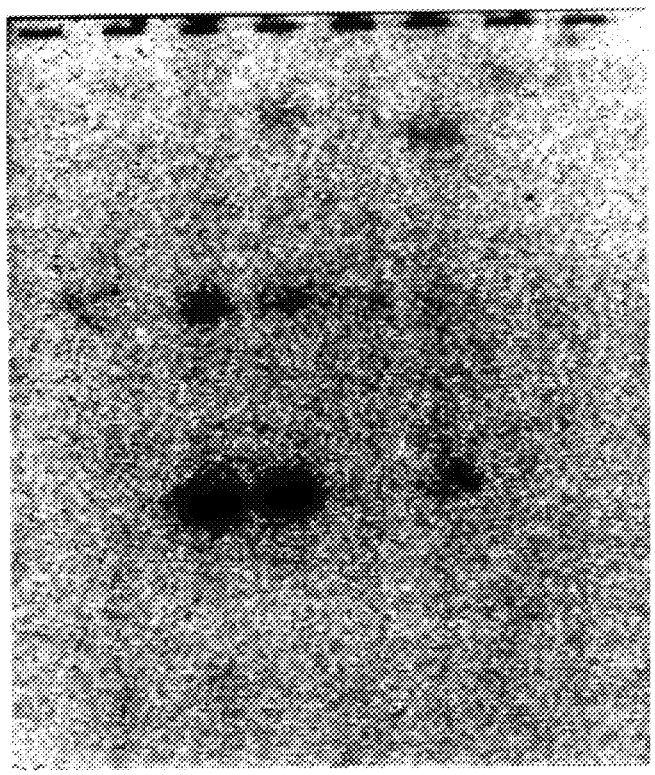

FIG. 6. Southern blot analysis of the AB1R cDNA. Lane A is EcoRI digested human DNA. Lane B is EcoRI digested mouse DNA. Lane C is HindIII digested mouse DNA. Lane D is HindIII digested human DNA. λ/HindIII markers were run to establish molecular weights.

Figure 7A:

FIGS. 7A and B. Representative autoradiographs of specific binding to rat brain sections at (A) anterior and (B) middle to posterior levels. The images were digitized and enhanced so that areas with higher levels of binding are lighter. Note that certain areas of the olfactory tubercle (lower part of sections in (A) and hippocampus (mid-lateral part of section in (B) stand out against the relatively uniform labelling of the rest of the grey matter.

Figure 7B:
Figure 8A:

FIGS. 8A and B. Representative autoradiographs of the in situ hybridization of the pAB1R antisense probe. section locations and method of reproduction are as in FIG. 7. Note the areas of high labelling (lightest areas) in the olfactory tubercle and hippocampus in agreement with the results from the binding autoradiography (FIG. 7).

FIG. 9. Nucleotide sequence of cDNA insert of rat C100-R clone, AB2R [SEQ ID NO's: 9 & 10]. The EcoRI fragment from nucleotide 31 through nucleotide 409 was used to screen a human hippocampal cDNA library.

FIG. 10. Nucleotide sequence of rat C100-R clone [SEQ ID NO: 12]. The disclosed sequence is the result of cloning and sequencing of a number of overlapping rat cDNA clones. The * above nucleotide 686 represents the junction with the rat C100-R nucleotide sequence depicted in FIG. 4 (nucleotide 40).

FIG. 11. Nucleotide sequence of cDNA inserts of human C100-R clone [SEQ ID NO's: 13–18]. The nucleotide designated M is either A or C and the nucleotide designated K is either T or G.

FIG. 12A. Sequence homology between human C100-R and rat C100-R. Human #4.t3 sequence [SEQ ID NO: 17] is aligned with the rat C100-R sequence depicted in FIG. 9 starting at nucleotide 544 [SEQ ID NO: 9].

FIG. 12B. Sequence homology between human C100-R and rat C100-R. Human clone HABIR #1#4 [SEQ ID NO: 13] is aligned with the rat C100-R sequence depicted in FIG. 4, starting at nucleotide 182 [SEQ ID NO: 13].

FIG. 12C. Sequence homology between human C100-R and rat C100-R. Human clone #1#1T3 [SEQ ID NO: 13] is aligned with the rat C100-R sequence depicted in FIG. 4 starting at nucleotide 1868 [SEQ ID NO: 13].

5. DETAILED DESCRIPTION OF THE INVENTION

The present invention relates to the cloning and expression of the C100-R. The C100-R was initially characterized as a binding site, present on the surface of neuronally derived cells, that bound specifically to the amyloid peptide βAPP-C100. Expression of the βAPP-C100 amyloid peptide has been shown in animal models to correlate with the specific type of neuronal degeneration that occurs in Alzheimer's Disease. The C100-R produced herein may be used to evaluate and screen drugs and analogs of β-APP that may be used in the diagnosis and/or treatment of Alzheimer's Disease.

5.1. THE C100-R CODING SEQUENCE

The initial rat C100-R cDNA clone, designated λAB1R, was obtained by screening a λgt11 rat brain expression library with β-APP-C100 ligand labeled with $^{35}$S-methionine or a peptide epitope "flag" sequence as described in Section 6, infra. The initial clone, designated pABIR-rat, was found to contain a 1970 bp insert comprised of the nucleotide coding sequence and deduced amino acid sequence depicted in FIG. 4. [SEQ ID NO's: 1 & 2]. A corresponding cDNA clone has been deposited with the ATCC and assigned numbers described in Section 7, infra. Sequence analysis reveals that the clone encompasses the carboxy-terminal section of the gene and contains 1395 base pairs of coding sequence and 575 bp of 3' untranslated sequence (FIG. 4).

Using RNA prepared from rat brain and a primer specific for the most 5' end of the ABIR cDNA insert, first strand synthesis was performed in a reverse transcriptase reaction. Following second strand synthesis, the cDNA was inserted into the bacterial Bluescript plasmid (Stratagene). Additional rat C100-R cDNA clones were isolated and sequenced (FIG. 9 [SEQ ID NO's: 9 & 10] and FIG. 10 [SEQ ID NO: 11]. The new sequences overlap with those rat sequences shown in FIG. 4 and extend the coding region towards the amino-terminal end of the C100-R protein (FIG. 10). The sequence disclosed in FIG. 9 diverges upstream of nucleotide 106 from the rat sequence shown in FIG. 10, indicating that alternatively spliced mRNAs may exist for the C100-R clone.

A search of the Genebank nucleotide sequence data base for homologies to the C100-R reveals a number of matches with the "B" type calcium channels [SEQ ID NO's: 6–8], the Ryanodine calcium channel, and the high affinity calcium binding protein, calreticulin [SEQ ID NO's: 4–5] (FIG. 5). The homology shared between C100-R and calcium channels is consistent with the unusual pH dependence of binding and the observation that disruption of calcium levels in neurons, particularly in cortex and hippocampus, results in neurotoxicity. The cDNA sequence of C100-R also contains homologies to the SER/THR Kinase "signature" or conserved catalytic core sequence described by Hanks et al. (1988, Science 241:42–52) FIG. 4 [SEQ ID NO: 2].

As indicated by the detection of an 11 Kb C100-R mRNA on Northern blots, the nucleotide sequence depicted in FIG. 4 is only a partial representation of the C100-R gene. Full length rat C100-R cDNA sequence may be obtained using a number of different methods. For instance, probes specific for the most 5' sequence of the rat clone may be used to rescreen the rat cDNA libraries. With each successful round of screening new 5' probes can be designed and used to reprobe libraries until the entire sequence has been obtained.

PCR technology may also be used to isolate the full-length rat C100-R gene. Using RNA prepared from an appropriate rat source, a primer specific for the most 5' end of the rat cDNA insert can be used to prime first strand synthesis in a reverse transcriptase reaction. The RNA/DNA hybrid can then be "tailed" with guanines using terminal transferase, digested with RNAase H, followed by second strand synthesis primed with a poly-C primer. By using primers with specific restriction sites incorporated into them, these "clone-specific" cDNAs can be easily inserted into an appropriate plasmid vector and sequenced.

The invention also relates to C100-R genes isolated from other species, including humans, in which C100-R activity exists. Members of the C100-R family are defined herein as those receptors that bind βAPP-C100 or fragments of the peptide. Such receptors may demonstrate about 80% homology at the nucleotide level, and even 90% homology at the amino acid level in substantial stretches of DNA sequence. A bacteriophage cDNA library may be screened, under conditions of reduced stringency, using a radioactively labeled fragment of the rat C100-R clone. Alternatively the rat C100-R sequence can be used to design degenerate or fully degenerate oligonucleotide probes which can be used as PCR probes or to screen bacteriophage cDNA libraries. A polymerase chain reaction (PCR) based strategy may be used to clone human C100-R. Two pools of degenerate oligonucleotides, corresponding to conserved motifs between the rat C100-R and calcium channels, may be designed to serve as primers in a PCR reaction. The template for the reaction is cDNA obtained by reverse transcription of mRNA prepared from cell lines or tissue known to express human APP-R. The PCR product may be subcloned and sequenced to insure that the amplified sequences represent the C100-R sequences. The PCR fragment may be used to isolate a full length C100-R cDNA clone by radioactively labeling the amplified fragment and screening a bacteriophage cDNA library. Alternatively, the labeled fragment may be used to screen a genomic library. For a review of cloning strategies which may be used, see E.g., Sambrook, 1989, Molecular Cloning, A Laboratory Manual, Cold Springs Harbor Press, N.Y.; and Ausubel et al., 1989, Current Protocols in Molecular Biology, (Green Publishing Associates and Wiley Interscience, N.Y.)

A cDNA library may also be constructed in a mammalian expression vector such as pcDNA1, that contains SV40 origin of replication sequences which permit high copy number expression of plasmids when transferred into COS cells. The expression of C100-R on the surface of transfected COS cells may be detected in a number of ways, including the use of a labeled ligand such as βAPP-C100 or a βAPP-C100 agonist labeled with a radiolabel, fluorescent label or an enzyme. Cells expressing the human C100-R may be enriched by subjecting transfected cells to a FACS (fluorescent activated cell sorter) sort.

In a specific embodiment described herein, an adult hippocampal cDNA library was screened with a labeled nucleotide fragment from the rat C100-R clone. The large EcoRI fragment, extending from nucleotide 31 through nucleotide 409 of the AB2R rat clone (FIG. 9 SEQ ID NO: 9) was used to probe the human cDNA library. Several clones were obtained and the cDNA inserts were sequenced. Human C100-R sequence is shown in FIG. 11 [SEQ ID NO's: 13–18], and regions of homology between the rat and human C100-R sequences are shown in FIG. 12 [SEQ ID NO's: 1, 9, 13, 15 & 17].

Any of the methods described above for isolation of full length rat C100-R clones may be used equally well for isolation of full length human C100-R clones. For instance, probes specific for the most 5' sequence of the human clone may be used to rescreen the human cDNA library. With each successful round of sequencing new 5' probes may be designed and used to reprobe libraries until the entire sequence has been obtained.

In accordance with the invention, nucleotide sequences which encode C100-R, fragments, fusion proteins or functional equivalents thereof, may be used to generate recombinant DNA molecules that direct the expression of the C100-R, or a functionally active peptide, fusion protein or functional equivalent thereof, in appropriate host cells. Alternatively, nucleotide sequences which hybridize to portions of the C100-R sequence may also be used in nucleic acid hybridization assays, Southern and Northern blot analyses, etc.

Due to the degeneracy of the genetic code, other DNA sequences which encode substantially the C100-R amino acid sequence, e.g., such as the rat sequence depicted in FIG. 4 or a functional equivalent may be used in the practice of the present invention for the cloning and expression of the C100-R. Such DNA sequences include those which are capable of hybridizing to the rat or human C100-R sequence under stringent conditions, or which would be capable of hybridizing under stringent conditions but for the degeneracy of the genetic code. The stringency conditions may be adjusted in a number of ways. For example, when performing polymerase chain reactions (PCR), the temperature at which annealing of primers to template takes place or the concentration of $MgCl_2$ in the reaction buffer may be adjusted. When using radioactively labeled DNA fragments or oligonucleotides to probe filters, the stringency may be adjusted by changes in the ionic strength of the wash solutions or by careful control of the temperature at which the filter washes are carried out.

Altered DNA sequences which may be used in accordance with the invention include deletions, additions or substitutions of different nucleotide residues resulting in a sequence that encodes the same or a functionally equivalent gene product. The gene product itself may contain deletions, additions or substitutions of amino acid residues within the C100-R sequence, which result in a silent change thus producing a functionally equivalent C100-R. Such amino acid substitutions may be made on the basis of similarity in polarity, charge, solubility, hydrophobicity, hydrophilicity, and/or the amphipatic nature of the residues involved. For example, negatively charged amino acids include aspartic acid and glutamic acid; positively charged amino acids include lysine and arginine; amino acids with uncharged polar head groups having similar hydrophilicity values include the following: leucine, isoleucine, valine; glycine, aniline; asparagine, glutamine; serine, threonine; phenylalanine, tyrosine. As used herein, a functionally equivalent C100-R refers to a receptor which binds to β-APP-C100 or fragments, but not necessarily with the same binding affinity of its counterpart native C100-R.

The DNA sequences of the invention may be engineered in order to alter the C100-R coding sequence for a variety of ends including but not limited to alterations which modify processing and expression of the gene product. For example, mutations may be introduced using techniques which are well known in the art, e.g. site-directed mutagenesis, to insert new restriction sites, to alter glycosylation patterns, phosphorylation, etc. For example, in certain expression systems such as yeast, host cells may over glycosylate the gene product. When using such expression systems it may be preferable to alter the C100-R coding sequence to eliminate any N-linked glycosylation site. In another embodiment of the invention, the C100-R or a modified C100-R sequence may be ligated to a heterologous sequence to encode a fusion protein. The fusion protein may be engineered to contain a cleavage site located between the C100-R sequence and the heterologous protein sequence, so that the C100-R can be cleaved away from the heterologous moiety.

In an alternate embodiment of the invention, the coding sequence of C100-R could be synthesized in whole or in part, using chemical methods well known in the art. See, for example, Caruthers, et al., 1980, Nuc. Acids Res. Symp. Ser. 7:215–233; Crea and Horn, 180, Nuc. Acids Res. 9(10):2331; Matteucci and Caruthers, 1980, Tetrahedron Letters 21:719; and Chow and Kempe, 1981, Nuc. Acids Res. 9(12):2807–2817. Alternatively, the protein itself could be produced using chemical methods to synthesize the C100-R amino acid sequence in whole or in part. For example, peptides can be synthesized by solid phase techniques, cleaved from the resin, and purified by preparative high performance liquid chromatography. (E.g., see Creighton, 1983, Proteins Structures And Molecular Principles, W. H. Freeman and Co., N.Y. pp. 50–60). The composition of the synthetic peptides may be confirmed by amino acid analysis or sequencing (e.g., the Edman degradation procedure; see Creighton, 1983, Proteins, Structures and Molecular Principles, W. H. Freeman and Co., N.Y., pp. 34–49.

5.2. EXPRESSION OF THE C100-R

In order to express a biologically active C100-R, the nucleotide sequence coding for C100-R, or a functional equivalent as described in Section 5.1 supra, is inserted into an appropriate expression vector, i.e., a vector which contains the necessary elements for the transcription and translation of the inserted coding sequence. The C100-R gene products as well as host cells or cell lines transfected or transformed with recombinant C100-R expression vectors can be used for a variety of purposes. These include but are not limited to generating antibodies (i.e., monoclonal or polyclonal) that bind to the receptor, including those that competitively inhibit binding and "neutralize" β-APP activity of βAPP or fragments of βAPP, and the screening and selection of β-APP analogs or drugs that act via the C100-R; etc.

5.2.1. EXPRESSION SYSTEMS

Methods which are well known to those skilled in the art can be used to construct expression vectors containing the C100-R coding sequence and appropriate transcriptional/translational control signals. These methods include in vitro recombinant DNA techniques, synthetic techniques and in vivo recombination/genetic recombination. See, for example, the techniques described in Maniatis et al., 1989, Molecular Cloning A Laboratory Manual, Cold Spring Harbor Laboratory, N.Y. and Ausubel et al., 1989, Current Protocols in Molecular Biology, Greene Publishing Associates and Wiley Interscience, N.Y.

A variety of host-expression vector systems may be utilized to express the C100-R coding sequence. These include but are not limited to microorganisms such as bacteria transformed with recombinant bacteriophage DNA, plasmid DNA or cosmid DNA expression vectors containing the C100-R coding sequence; yeast transformed with recombinant yeast expression vectors containing the C100-R coding sequence; insect cell systems infected with recombinant virus expression vectors (e.g., baculovirus) containing the C100-R coding sequence; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing the C100-R coding sequence; or animal cell systems infected with recombinant virus expression vectors (e.g., adenovirus, vaccinia virus) including cell lines engineered to contain multiple copies of the C100-R DNA either stably amplified (e.g., CHO/dhfr) or unstably amplified in double-minute chromosomes (e.g., murine cell lines).

The expression elements of these systems vary in their strength and specificities. Depending on the host/vector system utilized, any of a number of suitable transcription and translation elements, including constitutive and inducible promoters, may be used in the expression vector. For example, when cloning in bacterial systems, inducible promoters such as pL of bacteriophage $\lambda$, plac, ptrp, ptac (ptrp-lac hybrid promoter) and the like may be used; when cloning in insect cell systems, promoters such as the baculovirus polyhedrin promoter may be used; when cloning in plant cell systems, promoters derived from the genome of plant cells (e.g., heat shock promoters; the promoter for the small subunit of RUBISCO; the promoter for the chlorophyll a/b binding protein) or from plant viruses (e.g., the 35S RNA promoter of CaMV; the coat protein promoter of TMV) may be used; when cloning in mammalian cell systems, promoters derived from the genome of mammalian cells (e.g., metallothionein promoter) or from mammalian viruses (e.g., the adenovirus late promoter; the vaccinia virus 7.5K promoter) may be used; when generating cell lines that contain multiple copies of the C100-R DNA, SV40, BPV- and EBV-based vectors may be used with an appropriate selectable marker.

In bacterial systems a number of expression vectors may be advantageously selected depending upon the use intended for the C100-R expressed. For example, when large quantities of C100-R are to be produced for the generation of antibodies, vectors is which direct the expression of high levels of fusion protein products that are readily purified may be desirable. Such vectors include but are not limited to the E. coli expression vector pUR278 (Ruther et al., 1983, EMBO J. 2:1791), in which the C100-R coding sequence may be ligated into the vector in frame with the lacZ coding region so that a hybrid C100-R/lacZ protein is produced; pIN vectors (Inouye & Inouye, 1985, Nucleic acids Res. 13:3101–3109; Van Heeke & Schuster, 1989, J. Biol. Chem. 264:5503–5509); and the like. pGEX vectors may also be used to express foreign polypeptides as fusion proteins with glutathione S-transferase (GST). In general, such fusion proteins are soluble and can easily be purified from lysed cells by affinity chromatography, e.g., adsorption to glutathione-agarose beads followed by elution in the presence of free glutathione. The pGEX vectors are designed to include thrombin or factor Xa protease cleavage sites so that the cloned polypeptide of interest can be released from the GST moiety. See also Booth et al., 1988, Immunol. Lett. 19: 65–70; and Gardella et al., 1990, J. Biol. Chem. 265: 15854–15859; Pritchett et al., 1989, Biotechniques 7:580.

In yeast, a number of vectors containing constitutive or inducible promoters may be used. For a review see, Current Protocols in Molecular Biology, Vol. 2, 1988, Ed. Ausubel et al., Greene Publish. Assoc. & Wiley Interscience, Ch. 13; Grant et al., 1987, Expression and Secretion Vectors for Yeast, in Methods in Enzymology, Eds. Wu & Grossman, 1987, Acad. Press, N.Y., Vol. 153, pp. 516–544; Glover, 1986, DNA Cloning, Vol. II, IRL Press, Wash., D.C., Ch. 3; and Bitter, 1987, Heterologous Gene Expression in Yeast, Methods in Enzymology, Eds. Berger & Kimmel, Acad. is Press, N.Y., Vol. 152, pp. 673–684; and The Molecular Biology of the Yeast Saccharomyces, 1982, Eds. Strathern et al., Cold Spring Harbor Press, Vols. I and II.

In cases where plant expression vectors are used, the expression of the C100-R coding sequence may be driven by any of a number of promoters. For example, viral promoters such as the 35S RNA and 19S RNA promoters of CaMV (Brisson et al., 1984, Nature 310:511–514), or the coat protein promoter of TMV (Takamatsu et al., 1987, EMBO J. 6:307–311) may be used; alternatively, plant promoters such as the small subunit of RUBISCO (Coruzzi et al., 1984, EMBO J. 3:1671–1680; Broglie et al., 1984, Science 224:838–843); or heat shock promoters, e.g., soybean hsp17.5-E or hsp17.3-B (Gurley et al., 1986, Mol. Cell. Biol. 6:559–565) may be used. These constructs can be introduced into plant cells using Ti plasmids, Ri plasmids, plant virus vectors, direct DNA transformation, microinjection, electroporation, etc. For reviews of such techniques see, for example, Weissbach & Weissbach, 1988, Methods for Plant Molecular Biology, Academic Press, NY, Section VIII, pp. 421–463; and Grierson & Corey, 1988, Plant Molecular Biology, 2d Ed., Blackie, London, Ch. 7–9.

An alternative expression system which could be used to express C100-R is an insect system. In one such system, Autographa californica nuclear polyhidrosis virus (AcNPV) is used as a vector to express foreign genes. The virus grows in Spodontera frugiperda cells. The C100-R coding sequence may be cloned into non-essential regions (for example the polyhedrin gene) of the virus and placed under control of an AcNPV promoter (for example the polyhedrin promoter). Successful insertion of the C100-R coding sequence will result in inactivation of the polyhedrin gene and production of non-occluded recombinant virus (i.e., virus lacking the proteinaceous coat coded for by the polyhedrin gene). These recombinant viruses are then used to infect Spodoptera frugiperda cells in which the inserted gene is expressed. (E.g., see Smith et al., 1983, J. Viol. 46:584; Smith, U.S. Pat. No. 4,215,051).

In mammalian host cells, a number of viral based expression systems may be utilized. In cases where an adenovirus is used as an expression vector, the C100-R coding sequence may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing C100-R in infected hosts. (E.g., See Logan & Shenk, 1984, Proc. Natl. Acad. Sci. (USA) 81:3655–3659). Alternatively, the vaccinia 7.5K promoter may be used. (E.g., see Mackett et al., 1982, Proc. Natl. Acad. Sci. (USA) 79:7415–7419; Mackett et al., 1984, J. Virol. 49:857–864; Panicali et al., 1982, Proc. Natl. Acad. Sci. 79:4927–4931).

Specific initiation signals may also be required for efficient translation of inserted C100-R coding sequences. These signals include the ATG initiation codon and adjacent sequences. In cases where the entire C100-R gene, including its own initiation codon and adjacent sequences, is inserted into the appropriate expression vector, no additional translational control signals may be needed. However, in cases where only a portion of the C100-R coding sequence is inserted, exogenous translational control signals, including the ATG initiation codon, must be provided. Furthermore, the initiation codon must be in phase with the reading frame of the C100-R coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bitter et al., 1987, Methods in Enzymol. 153:516–544).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins. Appropriate cells lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERO, BHK, HeLa, COS, MDCK, 293, WI38, etc.

For long-term, high-yield production of recombinant proteins, stable expression is preferred. For example, cell lines which stably express the C100-R may be engineered. Rather than using expression vectors which contain viral origins of replication, is host cells can be transformed with the C100-R DNA controlled by appropriate expression control elements (e.g., promoter, enhancer, sequences, transcription terminators, polyadenylation sites, etc.), and a selectable marker. Following the introduction of foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the C100-R on the cell surface, and which respond to βAPP-C100 mediated signal transduction. Such engineered cell lines are particularly useful in screening for βAPP-C100 analogs.

A number of selection systems may be used, including but not limited to the herpes simplex virus thymidine kinase (Wigler, et al., 1977, Cell 11:223), hypoxanthine-guanine phosphoribosyltransferase (Szybalska & Szybalski, 1962, Proc. Natl. Acad. Sci. USA 48:2026), and adenine phosphoribosyltransferase (Lowy, et al., 1980, Cell 22:817) genes can be employed in tk⁻, hgprt⁻or aprt⁻cells, respectively. Also, antimetabolite resistance can be used as the basis of selection for dhfr, which confers resistance to methotrexate (Wigler, et al., 1980, Natl. Acad. Sci. USA 77:3567; O'Hare, et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neo, which confers resistance to the aminoglycoside G-418 (ColberreGarapin, et al., 1981, J. Mol. Biol. 150:1); and hygro, which confers resistance to hygromycin (Santerre, et al., 1984, Gene 30:147) genes. Recently, additional selectable genes have been described, namely trpB, which allows cells to utilize indole in place of tryptophan; hisD, which allows cells to utilize histinol in place of histidine (Hartman & Mulligan, 1988, Proc. Natl. Acad. Sci. USA 85:8047); and ODC (ornithine decarboxylase) which confers resistance to the ornithine decarboxylase inhibitor, 2-(difluoromethyl)-DL-ornithine, DFMO (McConlogue L., 1987, In: Current Communications in Molecular Biology, Cold Spring Harbor Laboratory ed.).

5.2.2. IDENTIFICATION OF TRANSFECTANTS OR TRANSFORMANTS THAT EXPRESS THE C100-R

The host cells which contain the coding sequence and which express the biologically active gene product may be identified by at least four general approaches; (a) DNA-DNA or DNA-RNA hybridization; (b) the presence or absence of "marker" gene functions; (c) assessing the level of transcription as measured by the expression of C100-R mRNA transcripts in the host cell; and (d) detection of the gene product as measured by immunoassay or by its biological activity.

In the first approach, the presence of the C100-R coding sequence inserted in the expression vector can be detected by DNA-DNA or DNA-RNA hybridization using probes comprising nucleotide sequences that are homologous to the C100-R coding sequence, respectively, or portions or derivatives thereof.

In the second approach, the recombinant expression vector/host system can be identified and selected based upon the presence or absence of certain "marker" gene functions (e.g., thymidine kinase activity, resistance to antibiotics, resistance to methotrexate, transformation phenotype, occlusion body formation in baculovirus, etc.). For example, if the C100-R coding sequence is inserted within a marker gene sequence of the vector, recombinants containing the C100-R coding sequence can be identified by the absence of the marker gene function. Alternatively, a marker gene can be placed in tandem with the C100-R sequence under the control of the same or different promoter used to control the expression of the C100-R coding sequence. Expression of the marker in response to induction or selection indicates expression of the C100-R coding sequence.

In the third approach, transcriptional activity for the C100-R coding region can be assessed by hybridization assays. For example, RNA can be isolated and analyzed by Northern blot using a probe homologous to the C100-R coding sequence or particular portions thereof. Alternatively, total nucleic acids of the host cell may be extracted and assayed for hybridization to such probes.

In the fourth approach, the expression of the C100-R protein product can be assessed immunologically, for example by Western blots, immunoassays such as radioimmuno-precipitation, enzyme-linked immunoassays and the like. The ultimate test of the success of the expression system, however, involves the detection of the biologically active C100-R gene product. A number of assays can be used to detect receptor activity including but not limited to β-APP binding assays; and β-APP biological assays using engineered cell lines as the test substrate.

5.2.3. RECOVERY OF THE C100-R

Once a clone that produces high levels of biologically active C100-R is identified, the clone may be expanded and used to produce large amounts of the receptor which may be purified using techniques wellknown in the art including, but not limited to immunoaffinity purification, chromatographic methods including high performance liquid chromatography, affinity chromatography using immobilized ligand such as β-APP-C100 or analogs thereof bound to beads, immunoaffinity purification using antibodies and the like.

Where the C100-R coding sequence is engineered to encode a cleavable fusion protein, purification may be readily accomplished using affinity purification techniques. For example, a collagenase cleavage recognition consensus sequence may be engineered between the carboxy terminus of C100-R and protein A. The resulting fusion protein may be readily purified using an IgG column that binds the protein A moiety. Unfused C100-R may be readily released from the column by treatment with collagenase. Another example would be the use of pGEX vectors that express foreign polypeptides as fusion proteins with glutathionine Stransferase (GST). The fusion protein may be engineered with either thrombin or factor Xa cleavage sites between the cloned gene and the GST moiety. The fusion protein may be easily purified from cell extracts by adsorption to glutathione agarose beads followed by elution in the presence of glutathione. In this aspect of the invention, any cleavage site or enzyme cleavage substrate may be engineered between the C100-R sequence and a second peptide or protein that has a binding partner which could be used for purification, e.g., any antigen for which an immunoaffinity column can be prepared.

5.3. GENERATION OF ANTIBODIES THAT DEFINE THE C100-R

Various procedures known in the art may be used for the production of antibodies to epitopes of the recombinantly produced C100-R. Neutralizing antibodies i.e., those which compete for the βAPP-C100 binding site of the receptor are especially preferred for diagnostics and therapeutics. Such antibodies include but are not limited to polyclonal, monoclonal, chimeric, single chain, Fab fragments and fragments produced by an Fab expression library.

For the production of antibodies, various host animals may be immunized by injection with the C100-R including but not limited to rabbits, mice, rats, etc. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium parvum.* by using any technique which provides for the production of antibody molecules by continuous cell lines in culture. These include but are not limited to the hybridoma technique originally described by Kohler and Milstein, (Nature, 1975, 256:495–497), the human B-cell hybridoma technique (Kosbor et al., 1983, Immunology Today, 4:72; Cote et al., 1983, Proc. Natl. Acad. Sci., 80:2026–2030) and the EBV-hybridoma technique (Cole et al., 1985, Monoclonal Antibodies and Cancer Therapy, Alan R. Liss, Inc., pp. 77–96). In addition, techniques developed for the production of "chimeric antibodies" (Morrison et al., 1984, Proc. Natl. Acad. Sci., 81:6851–6855; Neuberger et al., 1984, Nature, 312:604–608; Takeda et al., 1985, Nature, 314:452–454) by splicing the genes from a mouse antibody molecule of appropriate antigen specificity together with genes from a human antibody molecule of appropriate biological activity can be used.

Antibody fragments which contain specific binding sites of C100-R may be generated by known techniques. For example, such fragments include but are not limited to: the F(ab')$_2$ fragments which can be produced by pepsin digestion of the antibody molecule and the Fab fragments which can be generated by reducing the disulfide bridges of the F(ab')$_2$ fragments. Alternatively, Fab expression libraries may be constructed (Huse et al., 1989, Science, 246:1275–1281) to allow rapid and easy identification of monoclonal Fab fragments with the desired specificity to C100-R.

5.4. ANTI-SENSE RNA AND RIBOZYMES

Also within the scope of the invention are oligoribonucleotide sequences, that include anti-sense RNA and DNA molecules and ribozymes that function to inhibit the translation of C100-R mRNA. Anti-sense RNA and DNA molecules act to directly block the translation of mRNA by binding to targeted mRNA and preventing protein translation. In regard to antisense DNA, oligodeoxyribonucleotides derived from the translation initiation site, e.g., between −10 and +10 regions of the C100-R nucleotide sequence, are preferred.

Ribozymes are enzymatic RNA molecules capable of catalyzing the specific cleavage of RNA. The mechanism of ribozyme action involves sequence specific hybridization of the ribozyme molecule to complementary target RNA, followed by a endonucleolytic cleavage. Within the scope of the invention are engineered hammerhead motif ribozyme molecules that specifically and efficiently catalyze endonucleolytic cleavage of C100-R RNA sequences.

Specific ribozyme cleavage sites within any potential RNA target are initially identified by scanning the target molecule for ribozyme cleavage sites which include the following sequences, GUA, GUU and GUC. Once identified, short RNA sequences of between 15 and 20 ribonucleotides corresponding to the region of the target gene containing the cleavage site may be evaluated for predicted structural features such as secondary structure that may render the oligonucleotide sequence unsuitable. The suitability of candidate targets may also be evaluated by testing their accessibility to hybridization with complementary oligonucleotides, using ribonuclease protection assays.

Both anti-sense RNA and DNA molecules and ribozymes of the invention may be prepared by any method known in the art for the synthesis of RNA molecules. These include techniques for chemically synthesizing oligodeoxyribonucleotides well known in the art such as for example solid phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors which incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

Various modifications to the DNA molecules may be introduced as a means of increasing intracellular stability and half-life. Possible modifications include but are not limited to the addition of flanking sequences of ribo- or deoxy-nucleotides to the 5' and/or 3' ends of the molecule or the use of phosphorothioate or 2' O-methyl rather than phosphodiesterase linkages within the oligodeoxyribonucleotide backbone.

5.5. USES OF THE C100-R, DNA AND ENGINEERED CELL LINES

The C100-R DNA, antisense oligonucleotides and ribozymes, APP-R expression products, antibodies and engineered cell lines described above have a number of uses for the diagnosis and treatment of Alzheimer's Disease.

For example, the C100-R DNA sequence may be used in hybridization assays of biopsies or autopsies to diagnose abnormalities of C100-R expression; e.g., Southern or Northern analysis, including in situ hybridization assays. In therapeutic applications, antisense or ribozyme molecules designed on the basis of the C100-R DNA sequence may be utilized to block transcription and expression of the C100-R gene product. Alternatively, the C100-R DNA could be used in gene therapy approach to introduce the normal recombinant gene into the defective cells of an individual or to correct an endogenous mutation in order to reconstitute the C100-R and its function.

In another embodiment of the invention, antibodies specific for the C100-R may be used to determine the pattern of receptor expression in biopsy tissue, or for diagnostic imaging in vivo; in such applications, "neutralizing" antibodies may be preferred. For example, an antibody conjugated to an is imaging compound could be administered to a patient to "map" the locations and distribution of the C100-R in vivo.

In another embodiment of the invention, the APP-R itself, or a fragment containing its βAPP-C100 binding site, could be administered in vivo. The free C100-R or the peptide fragment could competitively bind to β-APP and inhibit its interaction with the native receptor in vivo.

In yet another embodiment of the invention, the engineered cell lines which express the entire C100-R or its ligand binding domain may be utilized to screen and identify active βAPP-C100 agonists or antagonists. Alternatively, cell lines that endogenously express the C100-R may be used for this purpose; e.g., neuroblastoma cell lines such as SK-N-MC as exemplified herein may be used. βAPP-derived peptides, other peptides, synthetic compounds, natural products, and other sources of potentially biologically active materials can be screened in the following manners. The ability of a test compound to inhibit the binding of βAPP-C100 (which can be labelled e.g., with $^{35}$Met or a "flag" sequence or detected with antibodies to the peptide) to the C100-R, and thus its potential to act as either agonists or antagonists may be measured. As a source of the receptor either whole C100-R-expressing cells homogenates, or subcellular fractions may be used. The binding may be measured using standard receptor binding techniques, such as those described in Section 6.1.3. The ability of agents to prevent, or mimic, the effects of βAPP-C100 on signal transduction responses in the C100-R-expressing cells may be measured. For example, responses such as changes in cytosolic concentrations of calcium, activation of specific protein kinases, altered secretion of hormones or neurotransmitters, modulation of second messenger production, or changes in cellular metabolism may be monitored. These assays may be performed in whole cells or membrane preparations using conventional techniques developed for these purposes. In engineered cells or cell lines that respond to the toxic effects βAPP-C100, the ability of substances to induce or prevent the toxicity may be measured. Toxicity may be monitored as described in the literature (Yankner et al., 1989, Science 245:417–420), or by other established techniques.

Transgenic animals that contain the C100-R DNA as the transgene may be engineered to determine the in vivo effects of the βAPP-C100 agonists or antagonists found in the above or other screens, or to profile other agents that are potentially therapeutic for Alzheimer's Disease.

Recently, computer generated models for ligandreceptor interactions have been developed, and in a specific embodiment of the invention, information derived from computer modeling of C100-R may be used for design of receptor agonist or antagonist. Changes made to C100-R sequences, using for example techniques for site directed mutagenesis, and expression of mutant receptors in cell lines may be used to further define the functional role of particular receptor regions and residues.

6. EXAMPLES

The subsection below describes the initial characterization of an APP binding protein expressed on neuronally derived cells and the cloning and sequencing of a complementary DNA representing part of the rat C100-R. The deduced amino acid sequence of C100-R reveals several motifs shared in common between "B" type calcium channels, Ryanodine calcium channels, calreticulin and protein Serine/Threonine Kinases.

6.1. MATERIAL AND METHODS

6.1.1. IN VITRO TRANSLATION OF FLAG-βAPP-C100

The following "flag" sequence-containing oligonucleotide [SEQ ID NO's: 19 & 20] was synthesized and inserted into pGEM7, ACC ATG GAC TAC AAA GAC GAT GAC GAT AAA TCG AT MET ASP TYR LYS ASP ASP ASP ASP LYS SER. (Immunex; Prickett et al. 1989 BioTechniques 7:580). In addition, prior to the MET codon, the ACC triplet gives a consensus sequence for eucaryotic translation start and the ClaI site after the flag sequence was added for cloning as was HindIII linker at the five prime end of the oligio. The pGEM7 flag construct was cut with SmaI and ClaI and the ClaI site was filled in. The BglII/SmaI fragment from βAPP-695 was cloned into this construct. Clones with the proper orientation were selected. This recombinant was utilized to make $^{35}$S-βAPP-C100 peptide in two ways. First, in the coupled transcription/translation system, TNT Coupled Reticulocyte Lysate System (Promega Corp.). Closed circular plasmid DNA was added to the lysate along with $^{35}$S-methionine (6 $\mu C_1$) following the recommended procedure. Second, in uncoupled reactions, the recombinant was linearized with Spe I, and 5 μg DNA was utilized to produce RNA in vitro (≈20–30 μg) following the manufacturer's protocol (Promega Corp.). 1–5 μg of this RNA was translated in either a wheat germ or rabbit reticulocyte translation system according to manufacturer's protocol (Promega Corp.). The in vitro translations either had one-tenth volume of 100 mM N-acetyl glucosamine (Sigma) added, and were aliquotted and frozen at −80° C., and dialyzed prior to use; were aliquotted and frozen directly, then dialyzed and spin column purified prior to use (Boehringer-Mannheim); or were affinity purified using the commercially available Flag Anti-body (CA$^{++}$-dependent binding M1 Ab, IBI) coupled to Affigel 10 (Biorad). Affinity chromatography was accomplished by passing the in vitro translations over the Affigel 10-coupled M1 antibody column (1 ml bed volume) equilibrated in PBS (120 mM NaCl, 2.7 mM KCl, 10 mM phosphate buffer, pH 7.4) with 0.5 mM CaCl$_2$. After thorough washing (5–10 column volumes), the peptide was eluted from the column with PBS with Na$_2$EDTA (2 mM). The peptide eluted as a sharp 0.7 ml peak. EDTA was removed by dialysis for use in binding or autoradiography. The flag-βAPP-C100 construct was sequenced and the product peptide from the in vitro translation analyzed for amino acid composition by mass spectroscopic techniques to confirm its identity.

6.1.2. CELL CULTURE

PC12 cells (ATCC) for the binding assays were grown in RPMI1640 supplemented with 10% heat-inactivated horse serum and 5% fetal bovine serum. T-175 flasks were seeded with 5×10$^5$ cells/ml in 60 ml of growth medium containing 10 ng/ml NGF. An additional 60 ml of this medium were added every 2 days until the cells were harvested (usually at 6 days). Where indicated, PC12 cells were cultured as above except in the absence of NGF. Cells were collected by centrifugation at 138×g for 8 minutes. The supernatant was discarded and the pellet resuspended in 5 ml of the growth medium. The cells were triturated 3 times through a 23 g needle attached to a 10 cc syringe to provide a single cell suspension or, at most, small cell aggregates. Trypan blue dye exclusion indicated that over 99% of the cells were viable.

SK-N-MC cells (ATCC) were grown in DME supplemented with 10% calf serum. The SK-N-MC cells were cultured as described for PC-12 cells except NGF is not included.

6.1.3. BINDING TO CELLS

For βAPP-C100 binding experiments, PC-12 or SK-N-MC cells grown and prepared as described above, were counted, collected by low speed centrifugation (138×g), and resuspended in phosphate-buffered saline (PBS, pH 7.4) with 1% BSA and 1% glucose (PBG). An 0.08 ml volume of the cell suspension, containing 2×10$^6$ cells, was mixed with 0.01 ml of $^{35}$S-βAPP-C100 and 0.01 ml of PBG, or PBG containing either unlabeled βAPP-C100 or its vehicle. For kinetic and inhibition experiments, the concentration of $^{35}$S-βAPP-C100 was either 25 pM or 50 pM. For saturation experiments, the ligand concentration ranged from 15 pM to 6 nM. The mixture was incubated at 4° C. for 3 hours, unless otherwise indicated. At the end of the incubation period, the cells were pelleted by centrifugation at 138×g for 90 sec, the supernatant (containing the unbound ligand) was removed, and 0.2 ml of fresh, ice-cold PBG was added. The cells and fresh buffer were briefly agitated, and again centrifuged and suspended in fresh, ice-cold buffer as above. Finally, the cells were pelleted by centrifugation, filtered through BSA (0.1%) treated filters and washed with 4 1-ml rinses of ice-cold PBS with 0.1% BSA. The duration of the period between resuspension of the cells in fresh, ice-cold buffer and filtration of the cells was less than 10 min. In the dissociation experiments, and to collect a sample of bound ligand, the cells were incubated in the buffer added as the second wash for up to 3 hours to allow the bound ligand to dissociate. The cells were then pelleted by centrifugation and the supernatant (containing the bound ligand that had dissociated) was removed. The cells were then rewashed and harvested as described above. Radioactivity retained by filters was measured by scintillation counting. Nonspecific binding was taken as that occurring in the presence of excess (3.2 nM to 18 nM) βAPP-C100. Saturation data were analyzed by computer using commercially available software. The binding model that best fitted the experimental data was determined by F-test (p<.05).

6.1.4. BINDING AUTORADIOGRAPHY

Sprague-Dawley rats were sacrificed by hypercapnia and placed on ice until their brains could be removed (less than an hour). The brains were rapidly frozen in isopentane chilled to −20° C. with dry ice and either used immediately or stored at −80° C. until use. The brains were affixed to the specimen holder of a cryostat and 25 μM coronal sections were collected onto gelatin-coated microscope slides. The sections were either frozen overnight at −80° C. or used immediately. The sections were air-dried at 4° C. and then preincubated with the binding buffer (PBS, 1% BSA) for 30 minutes at 4° C. This buffer was replaced by fresh buffer containing either the ligand alone ($^{35}$S-βAPP-C100, 0.01 nM) or the ligand with up to a 10-fold excess of unlabeled βAPP-C100 or its vehicle. The incubation was continued for 3 h at 4° C. The ligandcontaining buffer was then removed and the sections were washed twice with fresh buffer (15 min. and 1 min., 4° C.). The sections were then dipped into ice cold distilled water 10 times and dried under a stream of air at room temperature. The sections were then apposed to a sheet of X-ray film for a period of 1 to 14 days and the film developed. Some sections were stained with Cresyl violet for identification of brain region. The optical densities of regions of the autoradiographs were determined quantitatively using an image analysis system.

6.1.5. SCREENING FOR THE C100-R cDNA BY EXPRESSION CLONING cDNA was constructed from embryonic day 18 rat brain mRNA according to the protocol of Neve et al. (1986; delineated in detail by Klickstein and Neve in *Current Protocols in Molecular Biology*). λgt11 libraries (rat brain cDNA library, RL Neve; human brain cDNA library, Clontech) were plated on Y1090 *E. coli* cells at 150,000 pfu/150 mm plate. Plates were incubated at 42° C. for 3 h, at which time plaques were just visible. Plates were overlaid with Schleicher and Schuell 132 mm nitrocellulose filters which had been saturated with 10 mM IPTG (isopropyl-β, D-thiogalactoside) and slightly air dried. Plates were set at 37° C. for 3 hours, and the first filter removed and placed in TBS (50 mM Tris, pH 7.7, 150 mM NaCl). A second, duplicate IPTG-soaked nitrocellulose filter was placed on the plate surface and left for two hours. The second filter was removed and placed in TBS. The filters were allowed to sit in TBS without blocking agent for at least 12 hours and up to four days to allow refolding. Filters were blocked in TBS with 5% nonfat skimmed milk for periods ranging from 2 h to overnight. Filters were washed in binding buffer (50 m Tris-HCl, Ph 7.7, 50 mM NaCl, 2 mM MgCl$_2$, 1 mM Dithiothreitol). Filters were incubated with in vitro translated $^{35}$S-βAPP-C100 at 3 nM for two hours at 4° C. Three 3 minutes washes (4° C.) were used to remove nonbound labeled peptide: (i) binding buffer alone, (ii) binding buffer +0.1% NP40, and (iii) binding buffer. Filters were immediately removed from the wash and air dried. The processed filters were exposed to X-OMAT RP film with a screen at −70° C. for 6 days to two weeks. It was found that wet plates were necessary to get sufficient protein/plaque to get significant signal. Also, throughout the procedure it was necessary to plate many more phage than routinely required at the comparable stage of purification for nucleic acid probes.

Even when a "plaque"-pure phage population containing the βAPP-C100 binding protein site was plated as described above, only a low percentage of the plaques bound to the βAPP-C100, possibly due to the requirement of proper folding for binding.

Duplicate filters were compared to identify plaques expressing protein which bound to the $^{35}$S-βAPP-C100. Positive plaques were picked and taken through further rounds of binding and purification. Six rounds of isolation were required to obtain a single positive clone from a rat brain cDNA library. This rat clone is designated λAB1R. Five rounds of isolation were required to isolate five positive clones from a human brain cDNA library.

The insert from λAB1R was subcloned by PCR amplification using λgt11 sequencing primers which include restriction enzyme sites (Sal I and Not I). The amplified fragment was purified, cut with the restriction enzymes as per manufacturer's specifications and subcloned into SalII/NotI-cut Bluescript (SK+, Stratagene). The rat subclone was designated pAB1R-rat.

A second cloning strategy was developed utilizing the commercially available antibody to the "flag" tag. Libraries were plated, filter lifts produced, processed, probed and washed as described above with the exception that the βAPP-C100 was not labeled with $^{35}$S-methionine. Filters were cross-linked in a Stratalinker cross-linker (Stratagene) and blocked by 2 h incubation in TBS with 5% nonfat milk. The filters were then probed with a commercial anti-flag antibody at 10 μg/ml (M2, IBI) in TBS. Excess antibody was removed by three 10 minute washes in TBS (4° C.), with the middle wash solution supplemented with 0.1% NP40. Filters were incubated with a second antibody, goat anti-mouse IgG (heavy and light chain) biotin conjugate (NEN) in the same manner as with the first antibody. After washing, the filters were incubated with [$^{125}$I]-Avidin (NEN) at 0.5 μC$_1$/ml in binding buffer as above. The last three washes were in TBS with the middle wash including 0.1% NP40. Filters were air dried, and exposed to XOMAT-RP film with screen at −70° C. for 6 d to three weeks. Autoradiographs of the filters were compared for duplicates. Positive plaques were picked and carried through further rounds of screening.

Phage containing the human cognate of the βAPP-C100 binding protein were cloned by both the direct binding method and the flag-antibody method. These cDNAs have been subcloned and are being sequenced.

6.1.6. cDNA CHARACTERIZATION cDNAs were either subcloned into high copy plasmid vectors and transformed into bacteria or were amplified directly from the phage recombinants by the polymerase chain reaction. In the former case, double-stranded miniprep DNA was sequenced using Sequenase (U.S. Biochemicals); in the latter case, the PCR products were purified and sequenced with the femtomole sequencing system (Promega).

Sequencing of the clones was done by standard dideoxy methodology (Sequenase; USBiochem). Computer analysis was done primarily with GenePro (Riverside Scientific Enterprises) and PCGene (Intelligenics).

Southern transfers of human DNA or rat DNA (PC12) were probed with a $^{32}$P-labeled 260 bp fragment (EcoRI/ScaI) representing the 5' end of the AB1R cDNA. 8 μg of DNA was cut with various restriction enzymes, run on a 0.8% agarose gel, and transferred to nylon or nitrocellulose.

Northern analysis was carried out on total cellular RNA isolated with the guanidinium thiocyanate method (Chirgwin et al. 1979 Biochemistry 18 5294). Glyoxal gels, formaldehyde-agarose gels and dot blots were utilized to quantitate and evaluate the RNA under different conditions and from different sources (Tanzi et al., 1987, Science 235:880–884; Tanzi et al., 1988, Nature 331:528–530). RNA from PC12 cells treated with nerve growth factor for various periods of time, RNA from brains of patients with Alzheimer's Disease and Down's Syndrome, RNA from brain subregions, RNA from various developmental stages, etc. was run. Samples from AD or Downs brains were attained from the Children's Hospital (Boston) Pathology Dept. and from the McLean Hospital Brain Tissue Resource.

A lysogen of the 1985 bp AB1R cDNA in λgt11 was constructed in Y1089 by infecting Y1089 bacteria with the recombinant phage at a moi of 10,000:1, and identifying temperature sensitive clones from the unlysed bacteria. The lysogen was induced with heat and IPTG, and the resultant cell lysate resuspended in Laemmil gel sample buffer. A portion of the sample was electrophoresed on 10% PAGE, transferred to nitrocellulose, and incubated in successively more dilute concentrations of urea in PBS-Triton-X at 4° C. over two days after the method of Kageyama and Pastan (1989, Cell 59:815). Binding to $^{35}$S-βAPP-C100 was then carried out according to the protocol used for isolating the AB1R clone from the cDNA libraries, with the change that PBS instead of TBS was used.

The cDNA insert from λAB1R was subcloned into the mammalian expression vector pCDNA1 in the antisense orientation, and PC12 cells were transfected by electroporation. These transient cells were grown in DME media for 3 d, treated with NGF and tested for their ability to bind $^{35}$S-labeled βAPP-C100. Stable transfectant cells were selected for by the inclusion of G418 in the media and neomycin resistant cells were subsequently tested in the binding assay for their ability to bind the labeled βAPP-C100 after treatment with NGF.

6.1.7. IN SITU HYBRIDIZATION USING βAPP-C100 BINDING PROTEIN PROBE

Hybridization probes were prepared by labeling the pAB1R-rat construct linearized at various restriction sites. Anti-sense RNA probes were made from the plasmid template linearized at the NcoI site utilizing the T3 promoter of Bluescript, and sense-control RNA probes were made from the plasmid linearized at the BamHI site utilizing the T7 promoter of Bluescript. Probes were made in various ways. In vitro transcription was used to produce RNA probes. RNA was labeled with either $^{35}$S-UTP (Promega reagents) or Digoxigenin-UTP (Boehringer-Mannheim reagents). Digoxigenin-labeled DNA probes were produced by PCR (Lanzillo, 1991; M. McKenna and J. Carlson, personal communication); PCR primers were made to produce the appropriate fragments (Genosys Biotechnologies, Inc.).

Sections for in situ hybridization were prepared in the same manner as for binding autoradiography, only using RNAse free conditions. Prior to hybridization, the sections were given two 3 m washes with phosphate buffer (0.1M) containing glycine (0.75 g/ml) followed by two 15 m washes with phosphate buffer alone. They were then treated with proteinase K (1 μg/ml in 15 mM Tris-HCl, pH 7.5 and 15 mM EDTA) for 30 m at 37° C. and washed with acetic acid anhydride (0.25% in 0.1M triethanolamine, pH 7.5) for 10 m. This was followed by two 15 m washes with SSC (0.15M NaCl, 0.015M sodium citrate, pH 7.0) at twice its normal concentration (2×), defatting with EtOH and chloroform, and air drying. The hybridization probe, prepared as described above, was then placed onto the sections in a solution containing 50% formamide, 20× Denhardt's reagent, 300 μg/ml single stranded DNA, 150 μg/ml tRNA, 20 mM β-mercaptoethanol (BME), and 2× SSC. Coverslips were placed over the sections and hybridization solution and sealed to the slides with rubber cement. The hybridization was carried out overnight at 60° C. The coverslips were then removed and the sections were washed twice for 30 m at 60° C. with 4× SSC supplemented with 300 mM BME. Following this, they were treated with RNAse (20 μg/ml in 2× SSC, 20 m BME) for 30 m at 45° C. The sections were then washed four times with 2× SSC (60 m, 30 m, 30 m, and 30 m at 60° C.), washed one time with 1× SSC (30 m, 60° C.), and left overnight in 2× SSC. The following day the sections were quickly rinsed in 0.05M phosphate buffer and then distilled water. They were then air dried and placed in contact with X-ray film. The films were developed 1d to 2 weeks later and used to establish gross distribution of hybridized probe. Finer localization of the probe was achieved by coating the sections with a photoemulsion then developing the emulsion and measuring the grain densities over cell bodies in various brain regions.

6.1.8. CLONING OF THE FULL LENGTH RAT APP-4

In order to obtain the full-length C100-R the rat libraries are being screened with various probes made from pAB1R-rat. These probes are specific for the most 5' sequence of the rat clone. After more rat sequence is available, subsequent rounds of screening will utilize probes specific to the most 5' sequence available at each round of screening. In addition, a second rat-brain cDNA library was constructed in λZAP (Stratagene) with a primer specific for the 5' region of the cDNA insert. The library was constructed using the RACE (rapid amplification of cDNA ends) protocol (Frohmann et al., 1988, Proc. Natl. Acad. Sci. USA 85:8998–9002) with the following modifications: (1) The cDNA synthesis was primed with AB1RT3-1 or with AB1RT3-3, specific for the 3' UTR of the AB1R mRNA, instead of with oligo(dT). (2) The MRNA was denatured with methyl-mercury hydroxide prior to cDNA synthesis. (3) MMLV reverse transcriptase ("Superscript," Bethesda Research Labs) was used instead of AMV reverse transcriptase. (4) NotI adapters instead of EcoRI linkers were attached to the ends of the cDNAs so that no subsequent digestion of the cDNA was necessary before cloning. The cDNAs were cloned into NotI digested, and partially filled in λ ZAP II, to make two libraries of approximately $10^5$ cDNA clones each.This library will be screened with probes specific for the most 5' sequence available at each round of cloning.

Another approach to cloning the full-length gene will be to utilize PCR technology. Using hippocampal messenger RNA we will use a primer specific for the 5' end of the cDNA insert and perform the reverse transcriptase reaction. The RNA/DNA hybrid will then be "tailed" with guanines by terminal transferase, the RNA digested with RNAse H and the second strand primed with a poly-C primer. By using primers with restriction sites incorporated into them, these "clone-specific" cDNAs will be cloned and sequenced. The process will be repeated through multiple rounds until the entire 11 kb sequence has been attained (Frohmann et al., 1988, Proc. Natl. Acad. Sci. USA 85:8998–9002).

6.2. RESULTS

6.2.1. RADIOLIGAND BINDING

Because βAPP-C100 is toxic to NGF-differentiated PC12 cells, we tested the binding of the in vitro synthesized βAPP-C100 fragment to the surface of PC12 cells that had been treated with NGF (Kozlowski et al. 1992 J. Neuroscience 12:1679). $^{35}$S-βAPP-C100 binding to the differentiated PC12 cells was inhibitable by unlabeled βAPP-C100 (FIG. 1A). Similar results were obtained with the neuroblastoma cell line, SK-N-MC (see FIG. 1B).

In the NGF-treated PC-12 cells, the inhibitable fraction of the binding accounted for 40%–60% of the total binding.

The $IC_{50}$ value for the inhibitable binding was 1.7±0.7 nM (n=5). Inhibitable binding reached a maximum after 3 hours of incubation and was completely dissociable (FIG. 2). Saturation experiments indicated the presence of a single class of binding sites with a $K_d$ value of 0.81±0.37 nM, in approximate agreement with the $IC_{50}$ value determined above, and a $B_{max}$ value of 0.37±0.05 fmole/$10^6$ cells. Binding of $^{35}$S-βAPP-C100 to NGF-treated PC12 cells was not significantly inhibited by other peptides, including a number of tachykinins. In rat brain sections, the highest levels of specific binding were found in regions of the hippocampus and olfactory tubercle.

The amount of inhibitable $^{35}$S-βAPP-C100 binding was dependent upon the duration of exposure of the PC12 cells to NGF. PC12 cells that were not exposed to NGF showed little inhibitable binding, whereas those cultured in the presence of NGF for 4 or 6 days showed progressively greater amounts of binding. Another variable affecting binding was pH. The maximum amount of binding occurred at pH 7. Binding was only 25% of maximum at pH 6 and only 52% of maximum at pH 8.5.

To assess the stability of $^{35}$S-βAPP-C100 in the assay conditions, samples of both free ligand at the end of the incubation period (unbound) and ligand which had bound to the cells and been released were examined by SDS-polyacrylamide gel electrophoresis (PAGE). Before addition to the assay, most of the radioactivity was contained in a single band with an apparent molecular weight of 15 kDa. This represents monomer βAPP-C100. A small amount of material was also present in two additional diffuse bands. One migrated at approximately twice the molecular weight of the major band and possibly represents a dimer of βAPP-C100. The other band had a much higher molecular weight and may be an aggregate. The gel profile of the unbound ligand at the end of the incubation period was identical to that of the ligand before incubation, indicating that the ligand had not been degraded. Similarly, the ligand released from binding had the same profile as the ligand originally added, with the possible exception of a slight reduction in the amount of high molecular weight material. These data show that the binding of βAPP-C100 ligand does not cause its modification.

A mutation of the tyrosine in βAPP-C100, made to examine the importance of a consensus sequence for phosphotyrosine ($Tyr_{687}$ to Phe), produced a peptide that was not toxic to differentiated PC-12 cells. $Phe_{687}$-βAPP-C100 does not significantly inhibit $^{35}$S-βAPP-C100 binding at concentrations up to 14 nM (n=3), making it at least 20 times less potent a ligand at the βAPP-C100 binding site than the native form.

6.2.2. CLONING AND CHARACTERIZATION OF THE C100-R

The autoradiographic signals from the $^{35}$S-βAPP-C100 binding to λgt11 plaques induced to express protein in the late lytic cycle were atypical and variable. We used the XOMAT-RP high resolution film and long exposures in order to establish clear duplicates on the autoradiographs (FIG. 3).

The size of the cDNA insert of the rat clone, λAB1R, was 1970 bp. The complete sequence is given in FIG. 4 (SEQ. ID. NOS: 1–2). The sequence given includes a portion of the β-gal gene derived from the vectors, λgt11 and Bluescript. The clone's open reading frame is not in register with the β-Gal gene, so the clone is being expressed as a nonfusion protein. The ATG at position 175 has an adjacent sequence eight base pairs away that could serve as an *E. coli* ribosomal binding site, -AGAAA (the canonical site is AGGA). Translation of the open reading frame initiating at this Methionine would yield a protein of 407 amino acids with a molecular weight of 45,253D. Such expression would probably be a product of reinitiation and has been previously noted for expression of a 100-kD nonfusion protein (Yang C. H. Lambie, E. J., and Snyder, M. J. of Cell Biology 116: 1303–1317). Sequence analysis has revealed that the clone contains 1349 base pairs of the carboxyl-terminal section of the gene (1395 minus β-Gal sequence) and 575 base pairs of 3' untranslated region. Nucleic acid sequence analysis shows homology with "B" type calcium channels [SEQ ID NO: 3], the Ryanodine calcium channel [SEQ ID NO's: 6–8], and a high affinity calcium binding protein, calreticulin [SEQ ID NO's: 4–5] (FIG. 5). Analysis of the translated protein sequence reveals several potential phosphorylation sites (various kinase target sites, including cAMP- and cGMP-dependent protein kinases, protein kinase C, casein kinase II), potential N-glycosylation sites, potential N-myristoylation sites, tyrosine sulfatation sites, and a serine/threonine protein kinase specific signature. This ser/thr kinase "signature" or conserved catalytic core sequence is found in the AB1R clone from 304–316 in the translated sequence (FIG. 4 SEQ ID NO: 2). The signature fits the -[LIVMFYC]-x- [HY]-D [LIVMFY]-K-X(2)-N- [LIVMFC] consensus pattern found by Hunter and his colleagues (Hanks, S. K., Quinn, A. M., and Hunter, T. (1988) Science 241 42–52). In the rat AB1R clone the sequence is V-I-H-R-D-I-K-S-D-N-I-L-L. (FIG. 4 SEQ ID NO: 2).

A number of additional rat cDNA clones have been isolated and sequenced (FIG. 9 [SEQ ID NO's: 9 & 10]). The new sequence information extends, in the 5' direction, the coding region of C100-R represented in FIG. 4. The * above nucleotide 686 in FIG. 9 represents the junction with the rat sequence depicted in FIG. 4 at nucleotide 40.

Northern analysis demonstrates that the messenger RNA corresponding to this cDNA is highly expressed throughout the brain. The cDNA hybridizes to a prominent band at 11 kb and more weakly to bands at about 3 kb. There is an NGF-inducible hybridizing band in PC12 cells at 9.5 kb. There is also a 4.4 kb hybridizing band in PC12 cells that appears with prolonged culturing, as well as with NGF treatment. These more weakly hybridizing bands of lower molecular weights may represent cross-hybridization to messenger RNAs coding for molecules like calreticulin which demonstrate homology at the nucleic acid level. Northern analysis of RNA from Alzheimer's Disease brains indicate that the βAPP-C100 binding protein is not expressed at a higher or lower level than in controls.

Southern analysis of human and rat genomic DNA demonstrates that AB1R cDNA hybridizes to a small number of bands, which is consistent with the AB1R representing a single copy gene (FIG. 6). A strongly hybridizing 3.0 kb band was observed as well as two more weakly hybridizing bands, one at 8.5 kb and a high molecular weight band between 25 and 30 kb. depending on species.

6.2.3. IN SITU HYBRIDIZATION

Figure 8B:
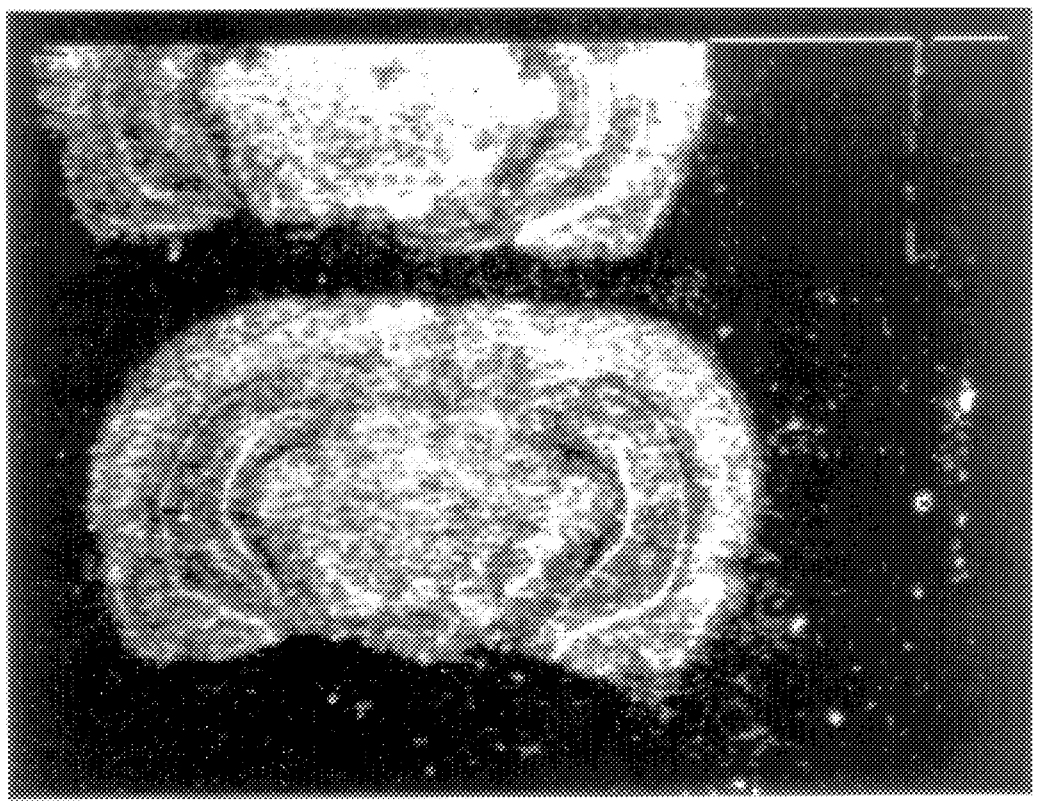

In rat brain section, levels of hybridization greater than background were obvious only in the hippocampus and olfactory tubercle (FIG. 8). This agrees with the distribution of binding sites as determined autoradioagraphically (FIG. 7).

7. EXAMPLE: CLONING OF HUMAN C100-R

An adult human hippocampal cDNA library in lambda ZAP 11 (Stratagene) was screened using a labeled fragment from the rat C100-R cDNA insert. The labeled fragment is represented as the EcoRI fragment, from nucleotide 31 through 409, in FIG. 9 [SEQ ID NO: 9]. The rat C100-R EcoRI fragment was labeled using a random priming reaction and the library was screened under stringent conditions using methods routinely employed by one skilled in the art. For a review of screening strategies see e.g. Sambrook 1989, Molecular Cloning, A Laboratory Manual, Cold Spring Harbor Press, N.Y. Several clones were obtained, ranging from 600 to 1500 base pairs in length. Results from partial sequencing of the 1500 base pair clone is shown in FIG. 11 [SEQ ID NO: 13–18]. Regions of sequence homology between the human C100-R sequence and the rat C100-R sequence are depicted in FIG. 12 [SEQ ID NO's: 1, 9, 13, 15 & 17].

8. DEPOSIT OF MICROORGANISMS

The following microorganisms have been deposited with the American Type Culture Collection, (ATCC), Rockville, Md. and have been assigned the following accession numbers:

| Microorganism | Date of Deposit | Accession No. |
|---|---|---|
| pABIR-rat | August 7, 1992 | 69047 |

The present invention is not to be limited in scope by the microorganisms deposited since the deposited embodiments are intended as illustrations of single aspects of the invention and any microorganisms which are functionally equivalent are within the scope of the invention.

The present invention is not to be limited in scope by the exemplified embodiments which are intended as illustrations of single aspects of the invention, and any clones, DNA or amino acid sequences which are functionally equivalent are within the scope of the invention. Indeed, various modifications of the invention in addition to those skilled in the art from the foregoing description and accompanying drawings. Such modifications are intended to fall within the scope of the appended claims.

It is also to be understood that all base pair sizes given for nucleotides are approximate and are used for purposes of description.

What is claimed is:

1. An isolated and purified C100R free of other mammalian proteins comprising the amino acid sequence of SEQ ID NO: 2.

2. An isolated and purified naturally occurring mammalian C100R, free from other mammalian proteins, that is encoded by a nucleotide sequence that hybridizes under high stringency conditions to the nucleic acid of SEQ ID NO: 1 and binds to the βAPP-C100 peptide.

3. A fusion protein comprising a naturally occurring mammalian C100-R, that is encoded by a nucleic acid sequence that hybridizes under high stringency conditions to the nucleic acid of SEQ ID NO: 1 and binds to the βAPP-C100 peptide, linked to a heterologous polypeptide.

4. An isolated and purified protein free from other mammalian proteins containing a C100-R serine/threonine kinase conserved catalytic core sequence comprising the following amino acids: VIHRDIXSDNILL (amino acids 304–316 of SEQ ID NO.2).

5. An isolated and purified C100-R peptide free from other mammalian proteins containing a C100-R serine/threonine kinase conserved catalytic core sequence comprising the following amino acids: VIHRDIKSNILL (amino acids 304–316 of SEQ ID NO. 2).

6. A fusion protein comprising a C100-R comprising the amino acid sequence of SEQ ID NO:2 linked to a heterologous polypeptide.

7. A fusion protein comprising a isolated C100-R polypeptide comprising the following amino acids: VIHRDIKSDNILL (amino acids 304–316 of SEQ ID No. 2), linked to a heterologous polypeptide.

* * * * *

UNITED STATES PATENT AND TRADEMARK OFFICE
CERTIFICATE OF CORRECTION

PATENT NO. : 5,854,392

DATED : December 29, 1998

INVENTOR(S) : Manly, et al

Figure 2A:
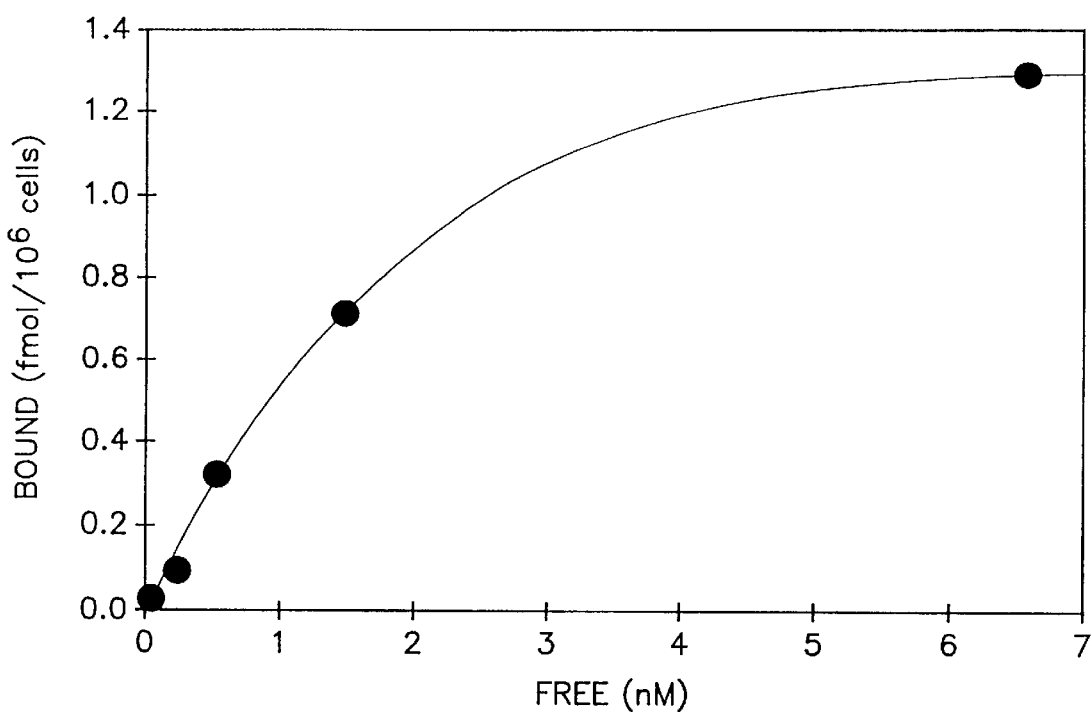
Figure 2B:
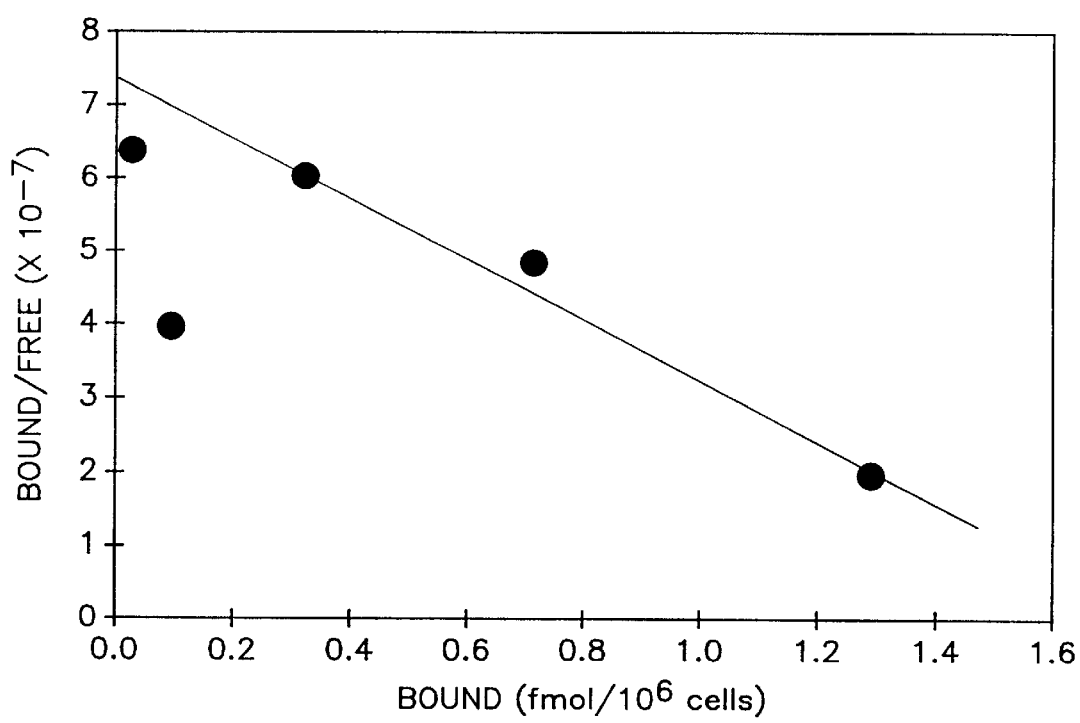

It is certified that error appears in the above-indentified patent and that said Letters Patent is hereby corrected as shown below:

Column 3, line 44, delete "FIG. 2." and substitute therefor -- FIGS. 2A-2B. -- and delete "(top panel)" and substitute therefor -- (FIG. 2A)--;

line 45, delete "(bottom panel)" and substitute therefor -- (FIG. 2B) --;
line 51, delete "FIG. 4." and substitute therefor -- FIGS. 4A-4C. --;
line 54, delete "FIG. 5A-C." and substitute therefor -- FIGS. 5A-5E. --;
line 55, delete "(A)" and substitute therefor -- (FIG. 5A) -- and delete "(B)" and substitute therefor -- (FIG. 5B)--; and
line 56, delete "(C)" and substitute therefor -- (FIGS. 5C-5E) --.

Column 4, line 7, delete "FIG. 7." and substitute therefor -- FIGS. 7A-7B. --; and
line 10, delete "(FIG. 7)" and substitute therefor -- (FIGS. 7A-7B) --.
line 19, delete "Figure 4" and substitute therefor -- Figure 4A --;
line 32, delete " SEQ ID NO. 13" and substitute therefor -- SEQ ID NO. 1 --.
line 34, delete " SEQ ID NO. 13" and substitute therefor -- SEQ ID NO. 15 --; and
line 36, delete " SEQ ID NO. 13" and substitute therefor -- SEQ ID NO. 1 --.

Column 14, line 41, delete "APP-R" and substitute therefor -- C100-R --.

Column 20, line 64, delete "(FIG. 1A)"; and
line 65, delete "(see FIG. 1B)" and substitute therefor -- (see FIG. 1) --.

Column 22, line 30, delete "Figure 9" and substitute therefor -- Figure 10 --; and
line 34, delete "Figure 4" and substitute therefor -- Figure 4A --.
In claim 4, line 4 of the claim, delete "VIHRDIXSKNILL" and substitute therefor -- VIHRDIKSDNILL --.

UNITED STATES PATENT AND TRADEMARK OFFICE
CERTIFICATE OF CORRECTION

PATENT NO. : 5,854,392
DATED : December 29, 1998
INVENTOR(S) : Manly, et al

It is certified that error appears in the above-indentified patent and that said Letters Patent is hereby corrected as shown below:

In claim 5, line 4 of the claim, delete "VIHRDIKSNILL" and substitute therefor -- VIHRDIKSDNILL --.

Signed and Sealed this

Twelfth Day of October, 1999

Attest:

Q. TODD DICKINSON

Attesting Officer

Acting Commissioner of Patents and Trademarks